US010453322B2

(12) United States Patent
Kaindl

(10) Patent No.: US 10,453,322 B2
(45) Date of Patent: Oct. 22, 2019

(54) PERSONAL SAFETY DEVICE, METHOD AND ARTICLE

(71) Applicant: Robert Kaindl, Redmond, WA (US)

(72) Inventor: Robert Kaindl, Redmond, WA (US)

( * ) Notice: Subject to any disclaimer, the term of this patent is extended or adjusted under 35 U.S.C. 154(b) by 0 days.

(21) Appl. No.: 15/543,198

(22) PCT Filed: Dec. 4, 2015

(86) PCT No.: PCT/US2015/064080
§ 371 (c)(1),
(2) Date: Jul. 12, 2017

(87) PCT Pub. No.: WO2016/114861
PCT Pub. Date: Jul. 21, 2016

(65) Prior Publication Data
US 2018/0005503 A1  Jan. 4, 2018

Related U.S. Application Data

(60) Provisional application No. 62/102,924, filed on Jan. 13, 2015, provisional application No. 62/109,414, (Continued)

(51) Int. Cl.
G08B 7/00        (2006.01)
G08B 21/02       (2006.01)
(Continued)

(52) U.S. Cl.
CPC .......... G08B 21/02 (2013.01); A41D 1/002 (2013.01); A61B 5/11 (2013.01); A61B 5/6804 (2013.01);
(Continued)

(58) Field of Classification Search
None
See application file for complete search history.

(56) References Cited

U.S. PATENT DOCUMENTS 5,370,566 A * 12/1994 Mitchell, Jr. ............. B63C 9/20
                                                   441/106
5,690,411 A * 11/1997 Jackman ................. A41D 13/01
                                                     362/103
(Continued)

FOREIGN PATENT DOCUMENTS

CN    103164926 A    6/2013
ES    2 416 579 A1   8/2013

OTHER PUBLICATIONS

Chinese Office Action, dated Mar. 20, 2019, for Chinese Application No. 201580077577.5, 15 pages. (w/ English Machine Translation).

Primary Examiner — Julie B Lieu
(74) Attorney, Agent, or Firm — Seed IP Law Group LLP

(57) ABSTRACT

An article of clothing includes user-protection circuitry, integrated into the article of clothing. The user-protection circuitry includes condition-detection circuitry, which, in operation, generates one or more indications related to an environment of the article of clothing. The user-protection circuitry also includes broadcast circuitry including at least one pulsing device, and control circuitry. The control circuitry, in operation, activates the broadcast circuitry based on the one or more indications related to the environment of the article of clothing generated by the condition-detection circuitry.

28 Claims, 7 Drawing Sheets

Related U.S. Application Data filed on Jan. 29, 2015, provisional application No. 62/160,824, filed on May 13, 2015.

(51) Int. Cl.

| | | |
|---|---|---|
| *A61B 5/11* | (2006.01) | |
| *A61B 5/00* | (2006.01) | |
| *A41D 1/00* | (2018.01) | |
| *G08B 7/06* | (2006.01) | |
| *G08B 5/00* | (2006.01) | |
| *G08B 6/00* | (2006.01) | |
| *G08B 21/22* | (2006.01) | |
| *B60Q 1/26* | (2006.01) | |
| *G08G 1/005* | (2006.01) | |
| *G08G 1/16* | (2006.01) | |
| *B60Q 1/52* | (2006.01) | |
| *A61B 5/01* | (2006.01) | |
| *A61B 5/0205* | (2006.01) | |
| *A61B 5/021* | (2006.01) | |
| *A61B 5/024* | (2006.01) | |
| *A61B 5/08* | (2006.01) | |

(52) U.S. Cl.
CPC ........... *B60Q 1/2673* (2013.01); *B60Q 1/525* (2013.01); *G08B 5/004* (2013.01); *G08B 5/006* (2013.01); *G08B 6/00* (2013.01); *G08B 7/06* (2013.01); *G08B 21/22* (2013.01); *G08G 1/005* (2013.01); *G08G 1/162* (2013.01); *G08G 1/164* (2013.01); *G08G 1/166* (2013.01); *A61B 5/01* (2013.01); *A61B 5/021* (2013.01); *A61B 5/024* (2013.01); *A61B 5/02055* (2013.01); *A61B 5/0816* (2013.01); *A61B 5/6805* (2013.01); *A61B 5/7445* (2013.01); *A61B 2503/22* (2013.01); *A61B 2560/0242* (2013.01); *A61B 2562/0257* (2013.01); *B60Q 2900/30* (2013.01)

(56) References Cited

U.S. PATENT DOCUMENTS

| | | | |
|---|---|---|---|
| 6,756,901 B2 * | 6/2004 | Campman | G08B 21/0415 340/539.1 |
| 9,013,290 B2 * | 4/2015 | Rigaud | B60Q 1/2676 340/441 |
| 9,168,862 B2 * | 10/2015 | Yang | A42B 3/0453 |
| 2002/0044052 A1 * | 4/2002 | Stewart | A41D 13/01 340/475 |
| 2003/0213045 A1 | 11/2003 | Fuentes | |
| 2005/0113167 A1 * | 5/2005 | Buchner | A63F 13/02 463/30 |
| 2005/0207138 A1 * | 9/2005 | Cheung | A43B 1/0027 362/84 |
| 2010/0253501 A1 * | 10/2010 | Gibson | A41D 13/01 340/475 |
| 2011/0130636 A1 * | 6/2011 | Daniel | G08B 25/016 600/301 |
| 2013/0240877 A1 | 9/2013 | Nishijima | |
| 2014/0176296 A1 * | 6/2014 | Morgan | G06F 3/011 340/4.13 |
| 2014/0370817 A1 * | 12/2014 | Luna | H04W 8/005 455/41.3 |
| 2015/0185045 A1 * | 7/2015 | Crawford | G01C 22/006 702/97 |
| 2015/0223731 A1 * | 8/2015 | Sahin | A61B 5/16 600/301 |
| 2015/0366275 A1 * | 12/2015 | Cserfoi | G08B 5/004 362/103 |
| 2016/0068214 A1 * | 3/2016 | Tang | B62J 6/00 362/108 |
| 2016/0370863 A1 * | 12/2016 | Jones | G06F 3/016 |
| 2017/0151989 A1 * | 6/2017 | Daniels | B62J 6/005 |
| 2017/0202275 A1 * | 7/2017 | St. John | A41D 27/10 |

\* cited by examiner

PERSONAL SAFETY DEVICE, METHOD AND ARTICLE

CROSS REFERENCE TO RELATED APPLICATIONS

This application claims the benefit under 35 U.S.C. § 119(e) to U.S. Provisional Application No. 62/102,924 filed Jan. 13, 2015, U.S. Provisional Application No. 62/109,414 filed Jan. 29, 2015, and U.S. Provisional Application No. 62/160,824 filed May 13, 2015, which applications are hereby incorporated by reference in their entireties.

BACKGROUND

Technical Field

The present disclosure relates to personal safety devices, methods and articles, such as articles of clothing and personal safety devices, which may be used, for example, to enhance personal safety.

Description of the Related Art

Currently, bicyclist, motorcyclist, pedestrians and police officers have limited ways to signal their presence and intended activities to motorists and others. Hand signaling, and, in the case of motorcyclist, conventional turn signals may be employed. Similarly, bicyclist, motorcyclist, pedestrians and police officers have limited ways to detect the presence and intended activities of motorists, and of other bicyclists, motorcyclists, pedestrians and police officers.

SUMMARY

In an embodiment, a system comprises: an article of clothing; and user-protection circuitry, integrated into the article of clothing, the user-protection circuitry including: condition-detection circuitry, which, in operation, generates one or more indications related to an environment of the article of clothing; broadcast circuitry; and control circuitry, which, in operation, activates the broadcast circuitry based on the one or more indications related to the environment of the article of clothing generated by the condition-detection circuitry. In an embodiment, the system comprises a wireless interface. In an embodiment, the system comprises a control terminal, which, to operation, transmits control signals to the user-protection circuitry. In an embodiment, the control circuitry configures the user-protection circuitry based on received control signals. In an embodiment, the broadcast circuitry comprises one or more of: one or more displays; one or more light emitting diodes (LEDs); one or more pulsers; one or more lasers; and one or more speakers. In an embodiment, the broadcast circuitry, in operation, silently broadcasts information to a wearer of the article of clothing. In an embodiment, the broadcast circuitry includes one or more pulsers and silently broadcasts information to a wearer of the article of clothing by activating the one or more pulsers. In an embodiment, activating one or more pulsers comprises activating the one or more pulsers in a pattern indicating to a wearer of the article of clothing at least one of: identification information related to one or more individuals; location information related to one or more individuals; motion information related to one or more individuals; information related to one or more hazards in a vicinity of or approaching the wearer of the article of clothing; and information providing instructions to the wearer of the article of clothing. In an embodiment, the identification information indicates whether the one or more individuals have been determined to be a friend or a foe of the wearer. In an embodiment, the condition-detection circuitry comprises one or more of: an accelerometer; a braking-condition sensor; a temperature sensor; a MEMS device; a microphone; a switch; a pulse-detector; an image capture device; and a communication interface. In an embodiment, the system comprises: a second article of clothing, which, in operation, communicatively couples to the user-protection circuitry. In an embodiment, the second article of clothing comprises at least one of: condition-detection circuitry, which, in operation, generate one or more indications related to an environment of the second article of clothing; and broadcast circuitry. In an embodiment, the article of clothing is worn by a first user and the user-protection circuitry coordinates broadcasting of information with user-protection circuitry of another article of clothing worn by a second user. In an embodiment, the broadcast circuitry, in operation, broadcasts, one or more of: a symbol indicating a braking condition of a wearer of the article of clothing; a symbol indicating a turning direction of the wearer of the article of clothing; a visual indication of a hazard; an indication of tracking of an approaching hazard; a symbol indicating a stop condition; instructions to one or more individuals approaching a wearer of the article of clothing.

In an embodiment, an article of clothing comprises: means for generating one or more indications related to an environment of the article of clothing; means for broadcasting information; and means for controlling the means for broadcasting information based on the generated one or more indications related to the environment of the article of clothing. In an embodiment, the means for broadcasting information broadcasts the information to the wearer of the article of clothing. In an embodiment, the means for broadcasting information comprises one or more of: one or more displays; one or more light emitting diodes (LEDs); one or more pulsers; one or more lasers; and one or more speakers. In an embodiment, the means for broadcasting broadcasts information indicating one or more of: identification information related to one or more individuals; location information related to one or more individuals; information related to one or more hazards; information providing directions or instructions to a wearer of the article of clothing; information to one or more individuals approaching the wearing of the article of clothing related to the environment of the article of clothing. In an embodiment, the indications related to the environment of the article of clothing indicate one or more of: a speed of a vehicle associated with a wearer of the article of clothing; a slowing of the vehicle; and an intended course of the vehicle.

In an embodiment, a method comprises: generating one or more control signals indicative of an environment of an article of clothing; and controlling user-protection circuitry embedded in the article of clothing based on the generated one or more control signals. In an embodiment, the method comprises generating at least one of the one or more control signals using a sensor embedded in the article of clothing. In an embodiment, the method comprises receiving a communication via a communication interface embedded in the article of clothing, wherein at least one of the one or more control signals is generated based on the received communication. In an embodiment, the received communication is a wireless communication received via a wireless communication interface embedded in the article of clothing. In an embodiment, the user-protection circuitry includes broadcast circuitry and the method comprises configuring the broadcast circuitry based on received control signals. In an embodiment, controlling the user-protection circuitry comprises one or more of: displaying information on a display; activating one or more light emitting diodes (LEDs); activating one or more pulsers; activating one or more lasers; and broadcasting audio on one or more speakers. In an embodiment, controlling the user-protection circuitry comprises silently broadcasting information to a wearer of the article of clothing. In an embodiment, the broadcast circuitry includes one or more pulsers and the controlling the user-protection circuitry comprises activating the one or more pulsers in a pattern indicating to a wearer of the article of clothing at least one of: identification information related to one or more individuals; location information related to one or more individuals; information related to one or more hazards in a vicinity of the wearer of the article of clothing; and information providing instructions to the wearer of the article of clothing. In an embodiment, the method comprises broadcasting information indicating whether one or more individuals have been determined to be a friend or a foe of a wearer of the article of clothing. In an embodiment, the generating one or more control signals comprises one or more of: generating an indication of an acceleration; detecting a braking-condition; sensing a temperature; receiving motion information from a MEMS device; receiving sound information from a microphone; receiving a signal from a switch; detecting a pulse; receiving signals from an image capture device; and receiving signals from a communication interface. In an embodiment, the method comprises: communicatively coupling user-protection circuitry of the article of clothing to user-protection circuitry of another article of clothing. In an embodiment, the another article of clothing comprises at least one of: condition-detection circuitry, which, in operation, generate one or more indications related to an environment of the second article of clothing; and broadcast circuitry. In an embodiment, the article of clothing is worn by a first user and the user-protection circuitry coordinates broadcasting of information with user-protection circuitry of another article of clothing worn by a second user. In an embodiment, the user-protection circuitry, in operation, broadcasts, one or more of: a symbol indicating a braking condition of a wearer of the article of clothing; a symbol indicating a turning direction of the wearer of the article of clothing; a visual indication of a hazard; an indication of tracking of an approaching hazard; a symbol indicating a stop condition; instructions to one or more individuals approaching a wearer of the article of clothing. In an embodiment, an article of clothing comprises user protection circuitry configured to implement any of the methods described herein.

BRIEF DESCRIPTION OF THE SEVERAL VIEWS OF THE DRAWING(S)

DETAILED DESCRIPTION

Figure 1:
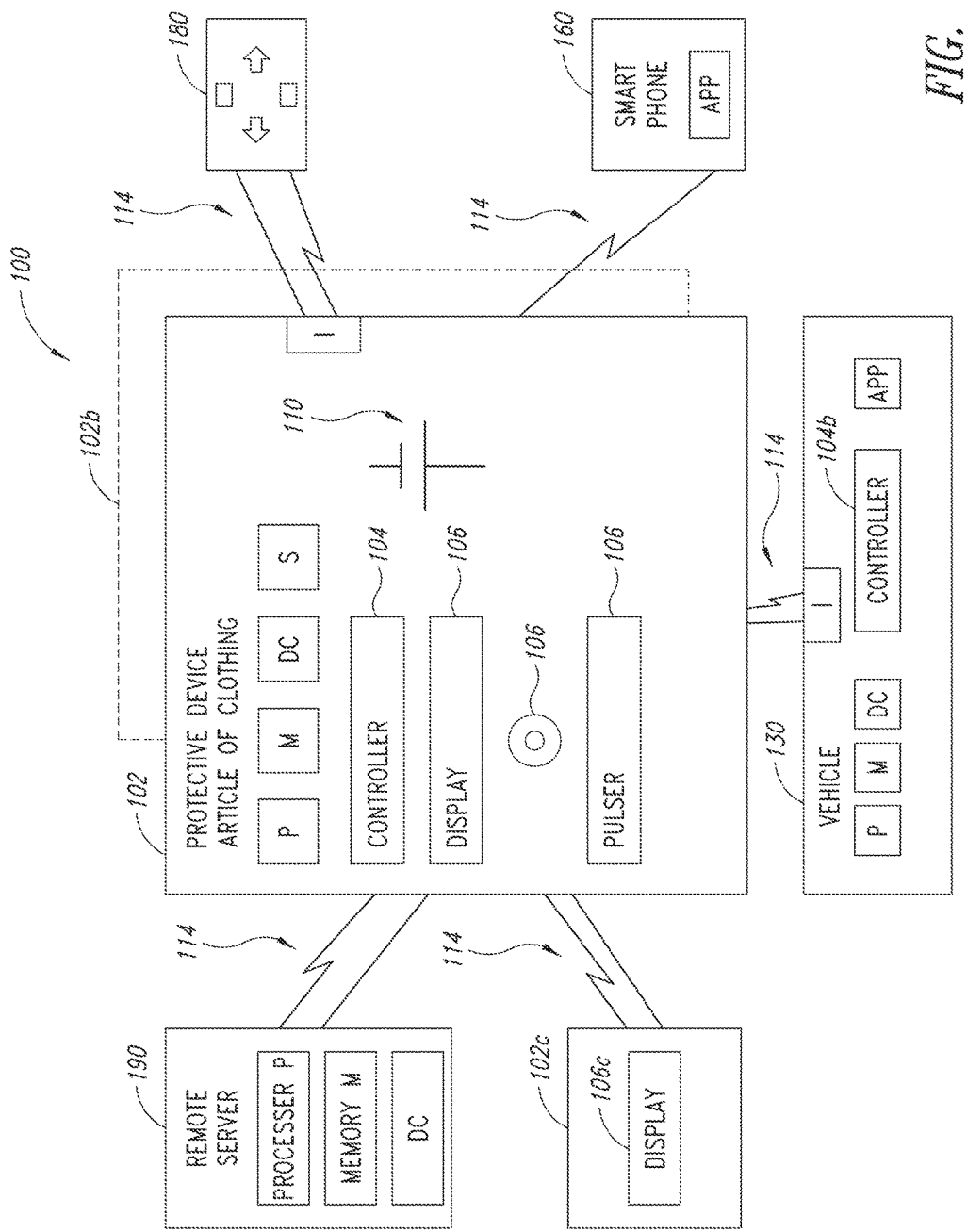
FIG. 1 is an example embodiment of an environment suitable for providing a protective device to a person.

In the following description, certain details are set forth in order to provide a thorough understanding of various embodiments of devices, systems, methods and articles. However, one of skill in the art will understand that other embodiments may be practiced without these details. In other instances, well-known structures and methods associated with, for example, display devices, pulsing devices, RFID device, controllers, clothing, etc., such as transistors, integrated circuits, etc., have not been shown or described in detail in some figures to avoid unnecessarily obscuring descriptions of the embodiments.

Unless the context requires otherwise, throughout the specification and claims which follow, the word "comprise" and variations thereof, such as "comprising," and "comprises," are to be construed in an open, inclusive sense, that is, as "including, but not limited to."

Reference throughout this specification to "one embodiment," or "an embodiment" means that a particular feature, structure or characteristic described in connection with the embodiment is included in at least one embodiment. Thus, the appearances of the phrases "in one embodiment," or "in an embodiment" in various places throughout this specification are not necessarily referring to the same embodiment, or to all embodiments. Furthermore, the particular features, structures, or characteristics may be combined in any suitable manner in one or more embodiments to obtain further embodiments.

The headings are provided for convenience only, and do not interpret the scope or meaning of this disclosure.

The sizes and relative positions of elements in the drawings are not necessarily drawn to scale. For example, the shapes of various elements and angles are not drawn to scale, and some of these elements are enlarged and positioned to improve drawing legibility. Further, the particular shapes of the elements as drawn are not necessarily intended to convey any information regarding the actual shape of particular elements, and have been selected solely for ease of recognition in the drawings.

FIG. 1 shows a functional block diagram of an embodiment of a system 100 to provide and operate a protective device, such as an article of clothing. As illustrated, the system 100 includes a protective device in a form of an article of clothing 102, such as, for example, a jacket, vest, shirt, pants, shorts, hat, etc., which may be worn by a user, a vehicle 130, such as a bicycle, a motorcycle, etc., which the user may operate, a smart phone 160, a control terminal 180, which may be, for example, integrated into the article of clothing 102 or communicatively coupled to the article of clothing 102, and a remote server 190. Embodiments of the system 100 may include more than one of the various illustrated components, may include additional components, or may not include all of the illustrated components. For example, some embodiments may not include a vehicle 130 or a remote server 190, some embodiments may combine the functionality of the control terminal 180 and the vehicle 130, some embodiments may employ multiple smart phones 160, some embodiments may include a card reader (not shown), etc., and various combinations thereof.

One or more communication links 114 communicatively couple the components of the system 100 to each other. The communication links 114 may be wired or wireless communication links (e.g., POTS links, Internet links, GSM links, LTE links, LAN links, 802.11n links, short distance communication links (e.g. Bluetooth™), etc.), and various combinations thereof. For example, as illustrated the article of clothing 102 is coupled to the control terminal 180 through a wired and a wireless link 114, and to a smart phone 160 through a short distance communication link. The communication links are not limited to the illustrated links.

For example, the remote server 190 may communicate with the article of clothing 102 through communication links with the smart phone 160.

The article of clothing 102 as illustrated includes a processor P, a memory M, discrete circuitry DC, a controller 104, an interface I, one or more broadcast devices 106, as illustrated a display, a speaker and a physical stimulation device, such as a pulser (e.g., a device which generates a repetitive pulse for a short duration of time), a sensor S and a power system 110. As discussed in more detail elsewhere, the controller 104 of the article of clothing 102 controls the broadcast devices 106, to broadcast messages, such as international traffic signals, intended actions, warning indicators, lights, pulses, etc., and various combinations thereof. In some embodiments, for example, the one or more broadcast devices 106 may provide audio and physical (e.g., vibrations, pulses, etc.), in addition to or instead of video functionality, and various combinations thereof. The sensor S may sense indications of, for example, a deceleration, an approaching vehicle or person, a vehicle, person or object in a path of the user, identification information or the lack thereof, sensed, transmitted or read from another person, vehicle or device, etc., and various combinations thereof. The sensor S may comprise one or more of an image capture device, an infrared sensor, a motion sensor, an accelerometer, and RFID tag reader, etc., and various combinations thereof. As discussed in more detail elsewhere herein, the controller 104 may control the one or more broadcast devices 106 based on sensed indications from the sensor S.

As discussed in more detail elsewhere, the controller 104 may be implemented, for example, by executing instructions stored in the memory M on the processor P, by using state machines or logic implemented, for example, with discrete circuitry DC, by using look-up tables, etc., and various combinations thereof. Embodiments of the article of clothing 102 may include additional components, may not include all of the illustrated components, etc., and various combinations thereof. For example, some embodiments of the article of clothing 102 may comprise multiple broadcast devices 106 (e.g., multiple displays, speakers, pulsers, etc.), multiple interfaces I, multiple sensors S, etc., and various combinations thereof. Embodiments may employ personal lighted safety technology and personally customizable visual, audio and physical broadcast system technology to uses in an article of clothing or personal protection device.

As illustrated in FIG. 1, the system 100 includes a second article of clothing 102b, which may have a similar configuration as the article of clothing 102 and may share other components with the article of clothing 102, or employ separate components (e.g., the second article of clothing 102b may have a separate controllers or may be controlled by the controller 104 of the article of clothing 102). As illustrated, the system 100 also includes a third article of clothing 102c, which has a broadcast device in a form of a display 106c integrated therein. Communication links 114 couple the third article of clothing 102c to the first article of clothing 102, which controls operation of the display 106c. For example, the system may have a first article of clothing, such as a jacket, with an integrated display, such as an LCD screen, and a second article of clothing, such as a pair of pants, with an integrated display, such as a set of LEDs, with the first article of clothing having a controller configured to control operation of the LCD screen and the set of LEDs.

The vehicle 130 may facilitate the operation of the article of clothing 102, such as by providing control signals, power, etc., and various combinations thereof. For example, the vehicle 130 may provide power to the article of clothing 102 through one or more wired or wireless links 114. As illustrated, the vehicle includes a processor P, a memory M, discrete circuitry DC, a controller 104b, an application APP and an interface I.

The control terminal 180 may be employed to facilitate configuring and/or controlling the article of clothing 102. For example, to create or modify a list of symbols available for display, to create or modify schedules of displays, such as flashing schedules, brightness levels, pulsing patterns, identification information (e.g., friend or foe identification codes), maximum and minimum volume levels, etc., and various combinations thereof.

As discussed in more detail herein, a user (such as a person wearing the article of clothing 102), may use an application, as illustrated an APP installed on the mobile phone 160 or the vehicle 130, to configure the one or more broadcast devices 106, for example to select symbols to be displayed by the display. For example, a user may download and install an application APP on the smart phone 160 which allows the user select a symbol for displaying from a list of symbols. The controller 104 of the article of clothing 102 may respond to an indication of a selection from an APP by displaying the symbol using the display 106, etc.

The following discussion provides a brief, general description of a suitable computing environment in which the embodiments described herein may be implemented. Although not required, various embodiments will be described in the general context of computer-executable instructions, such as program application modules, objects, or macros being executed by one or more electronic devices, such as a smart phone, a vehicle, a control terminal, a personal computer, a server, etc., and various combinations thereof. Those skilled in the relevant art will appreciate that various embodiments can be practiced with other computing system configurations, including other handheld devices, multiprocessor systems, microprocessor-based or programmable consumer electronics, networked personal computers (PCs), minicomputers, mainframe computers, virtual systems, and the like. Various embodiments can be practiced in distributed computing environments where tasks or modules are performed by remote processing devices, which are linked through a communications network. In a distributed computing environment, program modules may be located in both local and remote memory storage devices.

Figure 2:
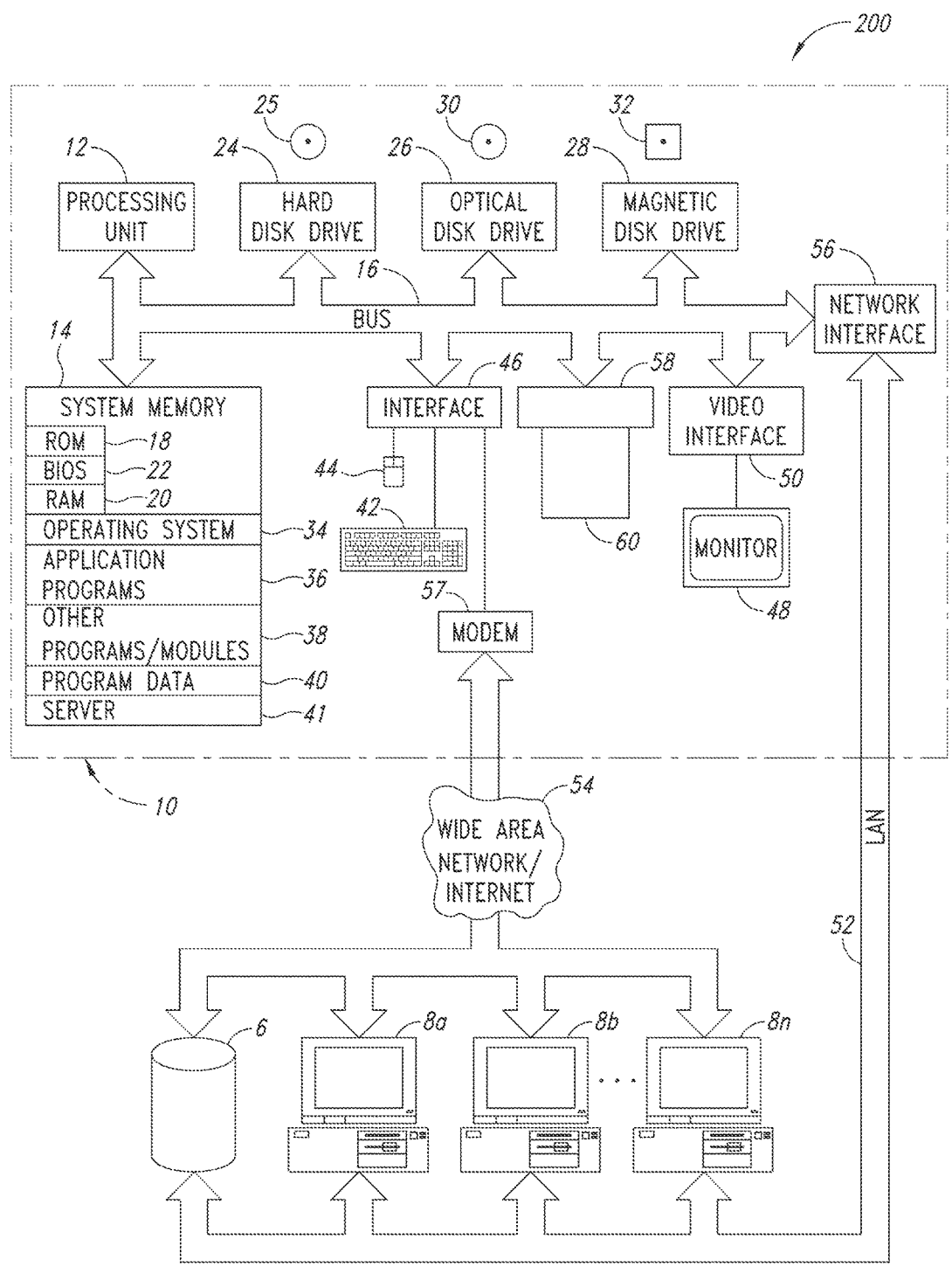
FIG. 2 is an example embodiment of an environment suitable for providing a protective device to a person.

FIG. 2 shows an embodiment of an environment 200 that may be employed to facilitate providing protective clothing as described herein. The environment 200 includes a computing system 10. For example, the computing system 10 may be configured as a display imbedded in an article of clothing, a smart phone, a control terminal, a local server, a host server, a communications server, etc. The computing system 10 may, for example, be operated by a user of a protective device, such as a user wearing an article of clothing, by a user to configure a protective device, such as an article of clothing, by a vendor of a protective device, such as a clothing provider, etc. The computing system 10 may take the form of any of the variety of types discussed above, which may run a networking client, for example a server, a Web browser, an application, etc. The computing system 10 comprises a processor unit 12, a system memory 14 and a system bus 16 that couples various system components including the system memory 14 to the processing unit 12. The processing unit 12 may be any logical processing unit, such as one or more central processing units (CPUs), digital signal processors (DSPs), application-specific integrated circuits (ASIC), etc. Unless described otherwise, the construction and operation of the various blocks shown in FIG. 2 are of conventional design. As a result, such blocks need not be described in further detail herein, as they will be understood by those skilled in the relevant art.

The system bus 16 can employ any known bus structures or architectures, including a memory bus with memory controller, a peripheral bus, and/or a local bus. The system memory 14 includes read-only memory ("ROM") 18 and random access memory ("RAM") 20. A basic input/output system ("BIOS") 22, which can form part of the ROM 18, contains basic routines that help transfer information between elements within the computing system 10, such as during startup.

The computing system 10 also includes one or more spinning media memories such as a hard disk drive 24 for reading from and writing to a hard disk 25, and an optical disk drive 26 and a magnetic disk drive 28 for reading from and writing to removable optical disks 30 and magnetic disks 32, respectively. The optical disk 30 can be a CD-ROM, while the magnetic disk 32 can be a magnetic floppy disk or diskette. The hard disk drive 24, optical disk drive 26 and magnetic disk drive 28 communicate with the processing unit 12 via the bus 16. The hard disk drive 24, optical disk drive 26 and magnetic disk drive 28 may include interfaces or controllers coupled between such drives and the bus 16, as is known by those skilled in the relevant art, for example via an IDE (Integrated Drive Electronics) interface. The drives 24, 26 and 28, and their associated computer-readable media, provide nonvolatile storage of computer-readable instructions, data structures, program modules and other data for the computing system 10. Although the depicted computing system 10 employs hard disk 25, optical disk 30 and magnetic disk 32, those skilled in the relevant art will appreciate that other types of spinning media memory computer-readable media may be employed, such as, digital video disks (DVD), Bernoulli cartridges, etc. Those skilled in the relevant art will also appreciate that other types of computer-readable media that can store data accessible by a computer may be employed, for example, non-spinning media memories such as magnetic cassettes, flash memory cards, RAMs, ROMs, SSDs, ReRAMs, smart cards, etc.

Program modules can be stored in the system memory 14, such as an operating system 34 (for example, Windows™, Android™, etc.), one or more application programs 36 (for example, an application to control a display of an article of clothing), other programs or modules 38, and program data 40. The system memory 14 also includes a server 41 for permitting the computing system 10 to exchange data with sources such as external controllers, Websites of the Internet, corporate intranets, or other networks, as well as other server applications on server computers. The server 41 may be markup language based, such as hypertext markup language (HTML), and operate with markup languages that use syntactically delimited characters added to the data of a document to represent the structure of the document, etc.

While shown in FIG. 2 as being stored in the system memory 14, the operating system 34, application programs 36, other program modules 38, program data 40 and server 41 can be stored on the hard disk 25 of the hard disk drive 24, the optical disk 30 and the optical disk drive 26 and/or the magnetic disk 32 of the magnetic disk drive 28, etc. A user can enter commands and information to the computing system 10 through input devices such as a keypad or keyboard 42 and a pointing device such as a mouse 44, a control pad mounted on a vehicle, etc. Other input devices can include a microphone, joystick, game pad, scanner, touch screen, card reader, chip reader, etc. These and other input devices as illustrated are connected to the processing unit 12 through an interface 46 such as a serial port interface that couples to the bus 16, although other interfaces such as a parallel port, a game port, a wireless interface, or a universal serial bus (USB) can be used. A display or monitor 48 or other display devices may be coupled to the bus 16 via video interface 50, such as a video adapter. The computing system 10 can include other output devices such as speakers, headphones, printers, etc.

The computing system 10 can operate in a networked environment using logical connections to one or more repositories 6 and/or other computing systems 8a-8n. While example embodiments may be discussed in terms of an example means of communication (e.g., WiFi, Bluetooth™), the computer system 10 may employ any known means of communications, such as through a local area network (LAN) 52 or a wide area network (WAN), a telecommunications network or the Internet 54. Such networking environments are well known and may include, for example, any type of telecommunications network or other network, such as CDMA, OFDMA, GSM, LTE, LTE-A, WiMAX, VoIP, WiFi, Internet Protocol, Bluetooth™, various IEEE standard protocols, etc.

When used in a LAN networking environment, the computing system 10 may be coupled to the LAN 52 through an adapter or network interface 56 (communicatively linked to the bus 16). When used in a WAN networking environment, the computing system 10 often includes a device, such as a modem 57, a mobile phone communication module or other device for establishing communications over the WAN/Internet 54. As illustrated, a modem 57 is shown in FIG. 2 as communicatively linked between the interface 46 and the WAN/Internet/Telecommunications network 54. In a networked environment, program modules, application programs, or data, or portions thereof, can be stored in a server computer (for example, another configured computing system similar to the computing system 10). Those skilled in the relevant art will readily recognize that the network connections shown in FIG. 2a are only some examples of establishing communication links between computers and/or other systems and devices, and other links may be used, including wireless links.

The computing system 10 may include one or more interfaces such as slot 58 to allow the addition of devices either internally or externally to the computing system 10. For example, suitable interfaces may include ISA (Industry Standard Architecture), IDE, PCI (Personal Computer Interface) and/or AGP (Advance Graphics Processor) slot connectors for option cards, serial and/or parallel ports, USB ports (Universal Serial Bus), audio input/output (I/O) and MIDI/joystick connectors, slots for memory, credit card readers, scanners, bar code readers, RFID readers, etc., collectively referenced as 60.

The term computer-readable medium as used herein refers to any medium that participates in providing instructions to processor unit 12 for execution. Such a medium may take many forms, including but not limited to, non-volatile media, and volatile media. Non-volatile media includes, for example, hard, optical or magnetic disks 25, 30, 32, respectively. Volatile media includes dynamic memory, such as system memory 14.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, as described herein, or any other medium from which a computer can read.

Various forms of computer readable media may be involved in carrying one or more sequences of one or more instructions to processor unit 12 for execution. For example, the instructions may initially be carried on a magnetic disk of a remote computer. The remote computer can load the instructions into its dynamic memory and send the instructions over a telephone line using a modem. A modem 57 local to computer system 10 can receive the data on the telephone line and use an infrared transmitter to convert the data to an infrared signal. An infrared detector coupled to the system bus 16 can receive the data carried in the infrared signal and place the data on system bus 16. The system bus 16 carries the data to system memory 14, from which processor unit 12 retrieves and executes the instructions. The instructions received by system memory 14 may optionally be stored on storage device either before or after execution by processor unit 12.

The repository 6 is a permanent storage medium for data. The repository 6 may be specific to each end user, or shared between some or all end users. For example, different vendors may have separate repositories or may share repositories. The repository 6 (only one illustrated) may run on the same computing system as an application accessing the repository, or on another computing system accessible over the network 52, 54.

Embodiments of the computing system 10 of FIG. 2 may not include all of the illustrated components of the computing system 10, may contain additional components not shown in FIG. 10, and may not be configured as shown in FIG. 10. For example, a computing system 10 configured as smart phone system (see FIG. 1), may not include an optical disk drive and may include an application specific integrated circuit or a digital signal processor (not shown) to perform one or more of the functions of the smart phone system. In another example, a smart phone system may include one or more telecommunications modules to handle call processing, such as CDMA, OFDMA, LTE, GSM, etc., call processing.

Figure 3:
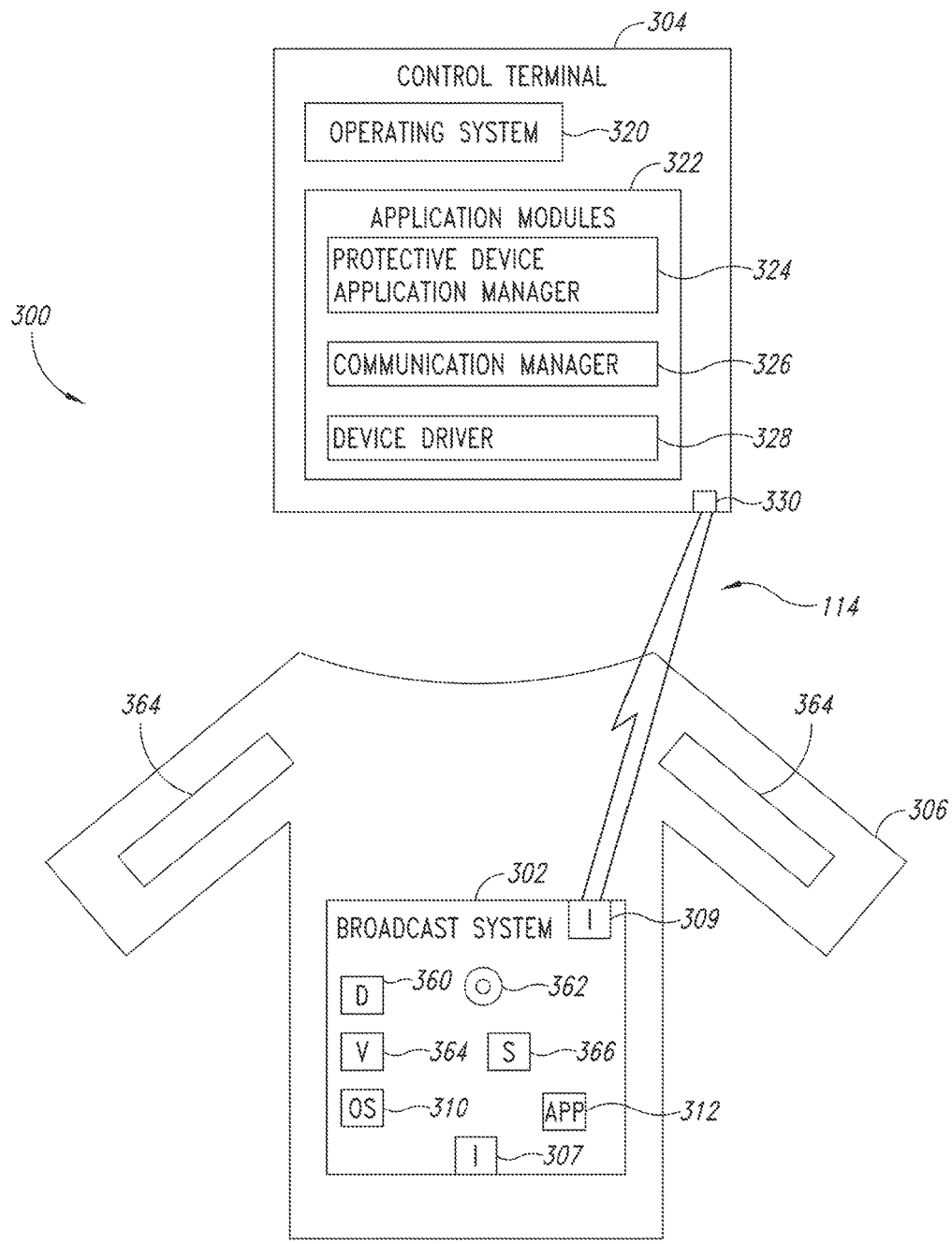
FIG. 3 is a functional block diagram of an embodiment of a system of a protective device.

FIG. 3 is a functional block diagram of an embodiment of a system 300 for providing a protective device 306, such as an article of protective clothing. The system 300 includes a broadcast system 302 and one or more control terminals 304. The broadcast system 302 is integrated into the protective device 306 and may comprise one or more displays 360, speakers 362, physical stimulation devices (e.g. vibrators, pulsers, heat strips, suction devices, pressure actuators, etc.) 364, sensors 366, communication interfaces I, power subsystems, etc., such as illustrated in an embodiment of the computing system 10 of FIG. 2 or the embodiment of the system 100 of FIG. 1. Similarly, the one or more control terminals 304 may comprise one or more configured computing systems, such as an embodiment of the computing system 10 of FIG. 2.

As illustrated, the audio/visual system 302 comprises an operating system 310 (for example, a Windows™, Android™, IOS™ operating system), and application modules 312 (for example, in a system memory, see system memory 14 of FIG. 2), such as a display application manager, a communication manager, and a device driver, which may, for example, control a USB interface 307, a wireless interface 309, etc. The wireless interface may include an antenna.

As illustrated, the one or more control terminals 304 comprise an operating system 320 (for example, a Windows™, Android™ or IOS™ operating system), and application modules 322 (for example, in a system memory, see system memory 14 of FIG. 2). As illustrated, the application modules 322 include a protective device application manager 324, a communication manager 326, and a device driver 328, which may, for example, control an interface 330, etc. The broadcast system 302 and the one or more control terminals 304 may communicate via wired or wireless communication links 114, via other communication networks (e.g., GSM, LTE, POTS), and various combinations thereof.

The protect device 306 may comprise, for example, vests, harnesses, coats, pullovers, covers, jackets, personal platforms, safety gear, safety clothing, armor, pants, shorts, shoes, sleeves, gloves, helmets, mobile devices, clothing inserts, etc., and various combinations thereof.

Embodiments of a system of providing protective devices, such as the embodiments of FIGS. 1 and 3, may utilize most/some national symbols and/or international symbols, designs, images for personal safety or to inform others with various programmable static or moving motion illuminated information. The intent is to inform, announce, display, project, signal critical information, desired information and/or traffic symbols including position lighting (brake lights, turn indicators/blinkers, position lights, warning lights) from the user's back and/or front chest surfaces and/or any other personal body part surfaces of users in order to protect the user and/or inform the user or others with information relating to actions or potential actions of the user or others. In some embodiments, the system may display, broadcast, advertise, convey information, light, etc. The information may take the form, for example, of warning messages, cheerful messages, etc. Broadcasting by an article of clothing may include audio, physical and visible light broadcasting using broadcasting devices embedded in the article of clothing.

Use of embodiments may reduce the very real possibility of users being killed, becoming victims in vehicle accidents, and suffering personal injuries. An embodiment may help a user to be seen or get noticed by others by using a highly visible lighting system during the day or night, or to notice others, etc. In an embodiment, users may display personal, customizable static or moving motion illuminated messages, if the user chooses.

One or more embodiments may be worn on any personal body surface capable of reflecting or illuminating detailed images or information that users may need to utilize, display, advertise, announce, proclaim, introduce, broadcast, inform, notify, light, cheer or warn others or receive warnings by providing desired, programmable static or moving motion illuminated information, audio information or physical stimulation, via, for example, vests, harnesses, coats, pullovers, covers, jackets, personal platforms, safety gear, safety clothing, armor, pants, shorts, shoes, sleeves, gloves, etc.

An embodiment comprises a vest/harness platform to display messages on the back and/or front surface of a user. An embodiment may appeal to the needs of users with complex safety features or simple static and programmable operating applications, and various combinations thereof. One or more embodiments may be upgradeable, such as through a download from a remote server (see FIG. 1). One or more embodiments may allow the user to also use the system at sporting events to promote and cheer their team along. One or more embodiments may provide illumination in front of or behind the user (e.g., a pedestrian, a bicyclist, a motorcyclist, etc., on darker trails, paths or walkways to provide lighting, or to increase the visibility of the user to others). In an embodiment, the system may be reversible or otherwise allow the user to reverse the vest/harness platform (e.g., from the back to the front chest), or to add additional displays (e.g., to double the footprint to include the front and back surfaces within the system) or other broadcast devices.

In one or more embodiments, the user may operate the system using handheld controllers or fixed controllers. In one or more embodiments, users may include police officers, flight-line services, search & rescue and military personnel. Control panels and display and audio messages may be customized for various users and purposes. Athletes, such as marathon runners, skiers or hikers, and other users may have protective articles of clothing customized for particular uses. For example, the display may positioned at a location on the body to increase visibility during a particular activity, a color scheme designed to be visible in certain conditions (e.g., colors visible in snow to facilitate rescuers locating an injured skier in the snow or colors providing better visibility in water for divers). Embodiments of an article of protective clothing may incorporate other customized protective features (e.g., extra padding, expandable air tubes, body armor, motion and/or tipping sensors, etc.). One or more embodiments may have upgradeable options, such as the ability to display sports team logos (e.g., football or soccer team logos), etc. Such options may be, for example, purchased initially or subsequently for an additional fee (e.g., a higher initial cost and/or downloadable for a fee). For example, a user may have the ability and choose to upgrade as they wish to add "Pick n Click" options (e.g., via a remote server website). In an embodiment, a user may be able to choose various additional accessories along with the ability to create customized static and/or moving motion designs for display by the system.

An embodiment may include lavish and ultra-high quality leather, Kevlar™ or Gor-Tex™ safety apparel materials. An embodiment may incorporate top-line safety apparel specific and may offer additional internal ridged components such as back plates, elbow pads, shoulder pads, knee pads and other fall and skid prevention safety features. An embodiment may be customized for specific applications, such as motorcyclist, police, military, airport flight-line services, etc. One or more embodiments may include back, front, sides, shoulders, sleeves, partial front and optional pants & helmet displays, speakers, and/or physical stimulation devices, controls and/or control leads if desired. An embodiment may allow the user to create a highly detailed custom designed application for different surfaces if desired. One or more embodiments may include the helmet attachments (e.g., broadcast devices and/or controls). One or more embodiments may monitor other signaling systems and generate a display based on the monitoring. For example, a system may monitor a conventional motorcycle signaling system and broadcast based on the monitoring. For example, if the conventional signaling system indicates the motorcycle is breaking, stopped or turning, etc., an embodiment may respond by displaying a large flashing red signal to warn other traffic, a stop sign, a large arrow indicating a direction, etc. One or more embodiments may monitor indications from a sensor and broadcast information based on the monitoring. For example, if a sensor indicates a user is slowing down, an embodiment may respond by displaying a large flashing red signal to warn other traffic. In another example, if a sensor indicates a vehicle is approaching the user from the left at a speed and trajectory which is likely to place the user at risk of injury, an embodiment may respond by broadcast an alert to the user, e.g., a pulse on the left side of a user's hand to indicate a danger is approaching from the left, etc. In response to an indication of an accident or a manual activation, an embodiment may broadcast location information, such as GPS location information, a location beam, etc.

One or more embodiments may be sold using incentives, such as medical insurance incentives, e.g., doubling the riders existing insurance up to a maximum for one year from date of original point of sale.

In one or more embodiments, users may have several options to control and program via remote or hardwired handheld controllers, hardwired body mounted controllers, Bluetooth™ wireless device controllers (iPhone™, Android™, personal device Apps, etc.) and other wired and wireless systems. In an embodiment, a custom programmable platform may utilize USB direct from a device, Bluetooth™ or some other wireless device format. One or more embodiments may employ various controller or programmable format options in various combinations.

In an embodiment, a user may have access to an online custom design center within a vendor website or directly through an App connected to the user's devices. This may facilitate providing the user with flexibility to make custom images, symbols, words or phrases into virtually up to 16 million different colors, any color pattern, format, light intensities, static or moving motion image or any lighting pulse speed rate controls the user desires. The custom creation may upload that information instantly to the device to copy then to upload directly to the protective device, such as an article of clothing. In an embodiment, there may also be a selection allowing the user to reboot the entire system to the original factory settings, if desired.

Embodiments may be configured for plug, choose, click and go operation. Embodiments may include baseline categories utilizing bright vests/harnesses in most single solid colored highly reflective options or multi-colored highly reflective options (e.g., Scotch-Light™ type reflective material). In an embodiment, a configuration may employ basic Yes/No options lists (e.g., international stop symbol? or USA national stop sign symbols?, etc.) and adjustable options such as the flashing pulse speed rates options, lighting intensity control to other pre-programmed and programmed preferred set-up choices, such as the examples discussed herein.

Embodiments may include control options in various combinations, such as the following example control options:

"Dim" Red Background always on selection (switchable off/on—square or round);

Stop sign selection (e.g., International stop sign with white or yellow horizontal strip or US standard stop sign);

Brakes or stop engaged selection (e.g., bright red circle with white strip or yellow strip);

Turn indicators engaged selection (Right & Left) (e.g., large flashing yellow amber arrows—Directional), with sub-options:
 a) Brakes disengaged (e.g., large flashing yellow amber arrow with "dim" red background on); and
 b) Brakes engaged (e.g., large flashing directional yellow amber arrow with brakes applied),
with "Opposite Flashing" bright red circle then yellow directional arrow, if desired;

Warning lights selection (e.g., bright red flashing triangle with exclamation point inside);

Hazard lights selection (e.g., bright red flashing triangle with exclamation point inside);

Caution Lights selection (e.g., bright yellow flashing triangle with exclamation point inside);

First aid selection (e.g., symbol bright green or background with white cross opposing flashing);

Star of Life selection (e.g., bright blue emergency medical service symbol flashing); and/or All clear selection (e.g., allowing the user to throw a dim or bright body light to illuminate in front of or behind to securely see ahead of or behind the user in the dark providing security and safety).

Some embodiments may allow the user to promote their favorite sports franchise, stadiums, sporting events, concerts or athletes. Some embodiments may allow (e.g., with a licensing fee to the sporting franchise, such as the NFL, NBA, etc.) users to create their own designs (e.g., by using a custom design center at a vendor's website) for these purposes.

Some embodiments may include options and functions plus more sophisticate systems allowing additional flexibility and customization.

In some embodiments, a controller may be connected directly to the receiver, such as a handheld controller or mounted controller. This controller may be hardwired or wirelessly remotely controlled. The hardwired handheld controller or mounted controller may provide the same functions as a handheld remote controller. The handheld device may provide physical safety features within its design as well, such as physical self-defense features (e.g., an alarm, whistle, pepper spray, tip sensor, etc.). The handheld platform may be designed to easily fit into the user's hand and may also house a series of small indicator lights to reassure the user that the system is working properly. The system may also perform a "Self Check" upon powering up. A rechargeable battery pack for the handheld unit may be independent to a rechargeable battery pack for the article of clothing (e.g., in a wireless embodiment). A hardwired rechargeable battery pack may be integrated within the system. The wireless handheld controller may broadcast an alarm if the article of clothing is too far away from the handheld control transmitter or when it doesn't receive a proper signal (e.g., an acknowledgment signal). This may reduce the possibilities of losing the handheld controller or false positives. An embodiment may draw power for the article of clothing and/or one or more control terminals from a vehicle (e.g., via a wired system power bus, a cigarette lighter sockets, electromagnet signals, etc.)

In an embodiment, a system may be customized for use with bicycles and other human-powered devices. An embodiment may employ integrated mounted sensor(s) connected to the bicycles braking levers (usually right hand side to the rear brakes) by an inconspicuous handbrake activation switch to engage and disengage lighting on the display to indicate braking activity. Wireless or wired links may be employed to communicatively couple the sensor(s) to the article of clothing.

An embodiment may employ independent finger toggle switches or buttons that are human activated (e.g., for the turn indicators, position lights, warning lights, etc.). The switched control terminal may be at the opposite side of the handlebars away from the brakes (usually left hand side). The control terminal transmitter housing unit may also have small indicator lights to assure the user that the system is working correctly by visually verifying proper operation. Embodiments may perform a self-check upon powering up. The system may be wireless and future upgrades and accessories may be implemented with a wireless platform in mind. One or more rechargeable battery packs may be mounted to the control terminal, the article of clothing, and/or the vehicle frame.

One or more embodiments may be customized for use with powered equipment, such as motorcycles and other powered vehicles. One or more wired connections may couple one or more system components (e.g., a control terminal, an article of clothing, etc.), to the equipment's internal wiring-harness, directly to control wire leads (e.g., by splicing onto a specific lighting indicator's source (brake lights, turn indicators, hazard wiring, etc.)), etc. A control terminal could be mounted onto the handlebars or hidden someplace inconspicuously. The control terminal housing unit may also have small indicator lights to assure the user that the system is working correctly by visually verifying proper function operations. The protective article of clothing system may be wireless or hardwired through the seat to the rider. If there is a passenger, the passenger may wear the protective clothing system to facilitate an unobstructed view from behind. The passenger and the operator may both wear protective clothing systems, which may be synchronized. A receiver may be located within the protective clothing system. A hardwired shielded magnetic quick-disconnect connecter may allow a continual positive trickle charge from the main power supply source to power charge a battery pack of the system while also being used. A power source on the protective clothing system may provide primary power to operate the entire system (e.g., the display system and the control terminals, etc.). The protective clothing system may be able to function for several hours independent of a trickle charge provided by the powered vehicle/equipment. The user may be able to choose one of multiple (e.g., three) direct contact point connections radially around the lower part of the system for ease of use to avoid wire entanglement, in a hardwired embodiment. The protective clothing system may be plugged into a converter to provide power from a power terminal (e.g., a 110-115 AC wall outlet to a 12V DC power converter) while not being used or away from a powered equipment's trickle charge system in order to charge both the transmitter and receiver components fully and completely. In an embodiment, multiple control terminals, multiple sensors and multiple articles of clothing, and various combinations thereof, may be employed.

In an embodiment, the display of a protective article of clothing may comprise, for example, LEDs, LED panels, LED plates, plasma plates, soft-image plates, image film, lighted display platform, reflective programmable surfaces, physical impulse sensors, etc., and various combinations thereof.

One or more embodiments may comply with various standards and safety protocols, such as those developed by or for the Motorcycle Safety Foundation (HSF), the Insurance Institute for Highway Safety (IIHS), the Insurance Institute if America (IIA), the American Insurance Association (AIA), the National Association of Insurance Commissioners (NAIC), various bicycle, motorcycle and ATV safety organizations, etc.

As discussed in more detail elsewhere herein, embodiments may be customized for use by various people and for various applications (e.g., motorcyclists, bicyclists, runners, pedestrians, sports fans, kids, police, military, firemen, security services, search & rescue services, other emergency personnel, flight Lines/tarmac (airport), recreational vehicles, hikers, skiers, scuba divers, etc., and various combinations thereof). For example, an embodiment may facilitate search and rescue workers looking for someone who is lost in the woods by proving lighting so the workers can see and be seen, by identifying other rescuers and search zones, etc.

Embodiments may be incorporated into ballistic and cut-proof undergarments, for example, in police and military embodiments discussed elsewhere herein.

Some embodiments may employ additional accessories (additional products), such as displays that expand around to the sides (turn indicators, position lights, etc.), to the front, such as yellow amber dim lighting similar to a car's wrap around position lights, headlights, etc. Some embodiments may be able to project an all clear or white light flood of light in an effort to illuminate the surroundings. Some embodiments may be configured to reduce night-blinding of the user and others (e.g., sensors and or controls may be employed to respond to an oncoming person or automobile and automatically dim or facilitate manual dimming of the lighting in response, shields may be employed to deflect lighting, etc.).

Some embodiments may provide flat fee licenses (e.g., to use sports team logos) and some embodiments may provide "Pay to Play" licenses. A user at a sporting event may be able to display their favorite athlete's number in the teams color or the actual team's logo in bright light on the user's front or back. The vest could be reversed from the back to the front or have a display on the front and back. Some embodiments may incorporate still cameras and/or video cameras. For example, a user may be able to take a selfie using the system, which may be automatically or manually posted to a website, etc.

In an embodiment, a helmet may employ a hardwired or a wireless transceiver (e.g., Bluetooth™) integrated into the system, or as an add-on. Hardwired versions may include quick disconnects, such as described elsewhere herein.

In an embodiment, for example, customized for police use, a blue "POLICE" may be displayed on the officer's backs in bright lights and their helmets possibly and sides might light up as well. A Blue/Red reverse pulsing image may be displayed while under pursuit. In an embodiment, a blue "POLICE" word with offsetting red stop sign & blue police titles may flash as desired. An embodiment may also provide extreme visual protection to the police officer when the police officer dismounts the police motorcycle or leaves the security of the police cruiser. The police officer may be provided lighting protection while outside or away from their vehicle and walking up onto the pulled over vehicle to announce the police officer's physical position to oncoming traffic. In an embodiment, a shielded trickle charger wire may automatically disconnect as the police officer exits their car or motorcycle, such as with the force of a small magnet. A beat officer may utilize a system with rechargeable battery and possible back-up batteries.

In an embodiment, for example, customized for use by a hiker, a display pattern to facilitate spotting by search & rescue in the day or night may be employed. For example, an embodiment may simulate a signal mirror in the daytime and a beacon at night.

In an embodiment, a plurality of protective systems may be configured to provide a coordinated protective broadcast system. For example, two or more users wearing separate protective clothing systems may desire to coordinate their displays. For example, two police officers at a crash scene, bicyclists riding together, a synchronized group of police officers displaying their message such as in a police line, a row of bicyclists as a peloton/pack in road race, a military platoon, encampment, movement operating as a single entity, etc., may wish to have their displays flash in unison or alternatively, a group of spectators at a sporting event (e.g., at a stadium, may wish to have the displays on their protective articles of clothing provide a joint display (e.g., each display showing part of a larger team logo display), etc.

In some embodiments, a display may be modified based on the location or relative position of a user or a plurality of users. For example, at a crash scene, it may be desired for the displays of officers and other emergency personnel may direct traffic in a certain direction. The system or systems may be configured to detect the positions of the officers and their display so as to select a display or set of displays to direct traffic as desired (e.g., to display an arrow directing traffic as desired (e.g., on one or a series of officers), to display flashing red on south facing displays and flashing yellow on north facing displays, etc.).

In an embodiment, people are empowered with the security of personal light safety technology. Several category platforms presented from a simple low cost introductory format comprising of a cell phone APP with simple display and control options up to the "Exclusive" high-end inclusive offerings. The embodiments may minimize human error in traffic accidents or individual incidences caused by visual impairments or inattentiveness. Depending upon the platform being utilized embodiments/technologies may be imbedded within leather, plastic, Kevlar™, or other fabrics. An embodiment's designs and technologies may be created to look fashionable and stylish with seamless hidden integrations about the garment, safety suit, jacket, host, pants or vest, etc.

In an embodiment, a visual crash avoidance and personal safety prevention system provides warnings, instructions as well as notices. An embodiment may provide the technology for avoiding injuries or death and assisting to simply be seen and/or be warned. An embodiment may launch an integrated multi-system or multi-vehicle communications capacity with active safety sharing device technologies to further increase the effort of safety on our roadways.

Baseline offerings may provide affordable versions of embodiments in order to appeal to initial users and helping developing countries' populations, for example, that use bicycles and scooters as primary modes of transportation. An embodiment may be APP centric driven and utilize simple Bluetooth™ or other connections from the controller, transmitter, laptop, a portable computer, iPad™, iPhone™ or other image display technology systems. These screen devices could be mounted or slide into a holder, cradle, clear plastic pouch or netted pocket connected to the back of the users while pointing the screens surface outward and/or backwards. This may facilitate notifying everyone of the user's location by being seen or viewed from behind. An APP embodiment may be controlled by the wireless device along with additional independent control transceiver systems (mounted or handheld accessories with brake solenoids, toggle switches, mini-controllers, etc.). A pocket designed to hold/contain a back mounted screen may contain an iPad or other system which may be utilized. This system may be added to a backpack of the user as well. In an embodiment, a baseline category" may be being introduced to allow the largest group of consumers the availability to be provided by personal lighted safety systems protection at a minimal cost. An embodiment may be provided as an APP centric driven application. An embodiment may provide users the opportunity to understand and realize how they may directly be benefiting themselves by minimizing human error effects from injury in their daily lives. A baseline category embodiment may utilize several present display options from cell phones, iPad's, laptops and miscellaneous display means either hardwired or wireless. An embodiment may be inexpensive, with a target pricing of, for example, $20 or less.

In an embodiment, a distress platform may be user activated and allow the user to initiate a panic button on the embodiment or via remote control to activate. In an embodiment, an additional benefit may be to send a GPS location instantly along with a series of various intense visual pulsing alerts of light within and throughout the system. In an embodiment, additional multi-angular directional highly noticeable laser light may be transmitted, e.g., a vertically erratic highly noticeable laser image signal beam of a first-aid green color. An embodiment may announce precisely the distressed user's location up into the sky to summon help to the GPS geographic coordinates. An embodiment may be programmed by default to contact the local 911, may be customized with the user's preferred contacts to call or transmit via a wireless network, etc. In an embodiment, the system application may allow users to manually input and initiate pre-programmed instructions to activate the visual embodiment display and to transmit GPS coordinates via cell phone. Audio alarms, tones and physical alarms could be utilized. Any message could be used if programmed or set prior to use otherwise a standard pre-programmed format may be used, which may be able to be overwritten or overridden. This system could utilize an emergency personal impact sensor system integrated into the system or through other devices such as cell phones or Bluetooth™ devices or other wireless systems.

In an embodiment, an emergency platform may automatically be initiated by the personal impact sensors being deployed and would an automatic response, such as the Emergency 911 contacting capabilities discussed above (e.g., by utilizing an existing cellular phone system via Bluetooth™ or pre-set-up emergency service for either announcing a multi-vehicle or single vehicle accident if riding a bicycle, motorcycle or incident if a pedestrian is involved with an occurrence with a vehicle, serious fall or another incidence). For example, if connected to an existing user's cell phone or using an embedded communication system, and embodiment may direct or guide emergency personnel to the injured user through a third party GPS cross-triangulation provider such as Google Maps™, AT&T™, etc. Additional fees may be charged for the service in some embodiments. The system may utilize an emergency personal impact sensor system integrated into the system or through other devices coupled to the system, such as cell phones, Bluetooth devices. GPS trackers or tracking may be employed in some embodiments to provide location information. In an embodiment, an emergency platform may be controlled, disconnected or turned off separately and independently, for example, by a very obvious red on/off switch adjusted by screwdriver. If the user disconnects the emergency portion of this system, that action will render the emergency system inoperative and the user's position simply won't be tracked or broadcast. In an embodiment, emergency system tracking may be inoperative until an emergency criteria is satisfied. For example, tracking may be disabled, and then activated in response to an indication that the user has been in an accident, such as a signal from an impact sensor, a body-tip sensor, etc.

In connection with an emergency and/or a distress platform, a vertical laser may be mounted behind one or both of the shoulders pointing nearly vertically into the sky in an embodiment. In an embodiment, compliance with appropriate regulations, such as aviation regulations, may be taken into consideration with regard to the timing, direction, and nature of a distress signal. In an embodiment, verifying vertical direction may be accomplished with a MEMS device, a mercury gravity switch or by an automatically activated electro-gyroscope to verify vertical unobstructed guidance of the laser pulse into the sky. In an embodiment, a laser lighting system may be provided, for example, in green laser international rescue colors and once automatically activated may provide an incremental pulse of movements with a digital fan effect into the sky from the laser manager. Such an embodiment may grab attention while allowing the rescuer or police to find and assist the distressed or injured user faster than using audio prompts without visual guidance or command assistance. In an embodiment, an all off button may allow a user or rescuer to turn off an emergency system once the user is located, for example, to avoid a distraction while providing aid to the user.

In an embodiment, a mayday signal may be transmitted in an emergency signal channel (e.g., 121.5 MHz, 243.0 MHz, etc.)

In an embodiment, a protective device may classify a person or vehicle in the vicinity of, approaching, or being approached by a user, and respond to the classification by taking appropriate action. For convenience, examples will be discussed in the context of a police operation, such as an operation to capture a suspect. A protective device may classify a person or vehicle by, for example, reading a transponder code, a squawk code, detecting the lack of a transponder code or squawk code, detecting the presence of a cell phone associated with a person or vehicle (e.g., a cell phone known to be used by a suspect), receiving a communication from another user's protective device (e.g., a communication indicating a suspect's route or another police officer's route), sensing a speed, a trajectory and a mass of the person(s) or vehicle, using face recognition software, mood recognition routines, etc., and various combinations thereof. The classification may include classification as a friend (e.g., classification as a police officer based, for example, on receipt of a transponder code or squawk code, which may including individual or group identification information), a foe (e.g., classification as a possible suspect, based, for example, on signals from one or more other protective devices, the lack of signals from one or more other protective devices, face recognition software, tracking software, etc., and various combinations thereof), a hazard (e.g., a vehicle approaching at an unsafe speed and trajectory), etc. A protective device may also classify sounds (e.g., gunshots, approaching vehicles, etc.).

A protective device may respond to a classification by signaling the user, for example silently or otherwise, of a classification of a person, vehicle or sound. For example, with reference to police officers, a protective device may cause a first vibration at a first speed and a first location to indicate another police officer is approaching from a first direction, and may cause a second vibration at a second speed and a second location to indicate a suspect or unknown individual is approaching from a second direction. The characteristics of the vibrations or other silent indicators (e.g., pressure, heat, suction, etc.) or non-silent indicators (e.g., sound) may be varied to provide indications of other information, such as a speed of approach (e.g. by varying a pulsing speed), a number of individuals approaching (e.g., by varying an intensity of the pulses), direction of approach (e.g., by varying a direction of the pulsing (e.g., from left to right to indicate individuals approaching from the left)), and whether the individuals are friends, foes, or unknown (e.g., by applying heat or suction as well as pulses); etc., and various combinations thereof. An embodiment facilitates notifying a user discretely of an approaching friend, foe or other threat, or innocents, so that the user is not surprised, and can adopt a strategy taking into account the information conveyed, for example, by silent indicators such as discussed herein. This may reduce, for example, the threat to a police officer from an approaching car or foe by providing the officer with useful information in a discrete manner.

Various sensors may also pickup electromagnetic radiation and detect metal, flesh (human or animal) target identification information in order to identify or classify approaching intruders, detect possible subterranean devices (e.g., hidden weapons) as the user approaches the target, or vice versa. An embodiment may collect radio or radar wave transmission energy identifiers as normally transmitted or reflected by coding from the target thus being determined as passive or active targets.

In an embodiment, a preemptive anti-collision incident alert protection system may be employed. The system may be configured to announce, identify and locate oncoming traffic through a series of physical actuators and sensors. An embodiment may have optional distance sensors and blind spot sensors or monitors with additional capabilities for functionality by intensifying the lighting controls by the embodiment with bright and dim flashing colors of choice as an automobile approaches (or other object) from behind or side quickly including close stops or tailgating the back of the user. In an embodiment, the system functions while being static, dynamic or while traveling. In an embodiment, the system's response may become more aggressive as the advance comes closer with a graduating frantic light pulse announcing the driver's location within a operators control system or the handlebars. The user may also be notified and provided with a visual blind spot sensors and monitors again while being static or dynamic. This may cue the user as to the fast moving closure rate by an automobile or other object that comes, for example, from behind or from the side. In an embodiment, a visual alert may be integrated into the control module that may be mounted onto the controller of the handlebar of a bicycle or motorcycle for clear viewing. In an embodiment, a vibrating alert system and a reactive light tracking may also be integrated into this alert. In other words, the light will appear to be targeting the approaching aggressive driver by visually tracking them.

In an embodiment, a vibrating alert system may provide physical touch vibrations, pulses, manipulations or stimulations with perceptible close proximity or direct contact of the skin or body parts with physical notifications or contact inputs. The vibrating alert system may directly contact or attract physical attention to a person's body from the precise direction of which the oncoming traffic is specifically approaching from. This is in order to alert the user of the specific direction requiring passive attention, short term attention or to be ready to take corrective actions and directional notice of a possible impact. Imbedded perimeter, outside radar, infrared, image or movement sensors may duplicate the direction of oncoming traffic internally by reflecting and initiating physical movement energy onto the user, for example, in the specific direction of an approaching threat (e.g., rearward for a danger approaching from the rear, on a side for a danger in a sideward blind spot).

Some embodiments may be directed to applications such as sports, military, police, etc. Sports and other function embodiments may remotely inform a football player to turn right then break straight then left because one or more remote-controlled actuators vibrated the right side, front then left retrospective of the football player's body instructing that player to move in those directions. The actuators may be incorporated into a belt or uniform. In an embodiment, a quarterback may go through a route and a remote controlled impulse mechanism would let the quarterback know to look left or right for a pass or to just run away onto safety in an alerted designated direction. In an embodiment, physical and visual direction indications may be transmitted then received by a user to advise and provide safety instructions by an instructor/operator to the player/user. An embodiment may be also used by police in large groups allowing an observer to direct an officer or a specific person through a crowd onto a target, such as a person of interest to the police. In an embodiment, the physical input sensors and output devices (e.g., accelerometers, switches, temperature sensors, pulsers, heating devices, speakers, microphones, suction devices, actuators, etc., and various combinations thereof) may be position on or in the vicinity of any desired body part and transmit/receive from any location on the body. Positions may be selected for various reasons, such as to provide more unobstructed access or visibility, better reception or transmission characteristics, etc.

An embodiment may facilitate police, for example, in very large groups, to control riots and other large crowds. For example, it may be desired for the police to communicate with each other indiscreetly, or discreetly. For example, an embodiment may be able to be change a display from all white, to all red or to any color combinations thereof. This may help the police identify a problem area to a specific individual, a small group or a quadrant within an entire brigade. An embodiment may be used to announce visibly to other officers that there might be officers in distress or that there is an area within a riot area where an individual or group of officers need assistance by transmitting an entire red embodiment color on an individual basis or quadrant area. Visual distresses or announcements may be responded to much faster than using a radio, then trying to figure out where the officer or officers are in a very large group. With a bright red light, it's simple and quick. In another embodiment, physical pulses providing directional information may be employed discreetly and incognito, while still facilitating a quick response time in directing officers to a problem area.

In an embodiment, a reactive light tracking system works with or independent of the vibrating alert system with a slight difference. Instead of notifying the user by vibrating the alert in a specific area of the user's body, the reactive light tracking system may track one or several oncoming vehicle(s) or persons with a series of intense lights seemingly appearing to be rotating around the user thus directing its focus and energy notifying the oncoming driver that they are being tracked. For example, if someone rides a bicycle up onto a user from behind or from the side that person will be visibly tracked and a series of lights will make it obvious. At the same time, the user may be provided with a signal indicating an approaching threat, such as pulses indicating a direction of the approaching threat. In other words, in an embodiment, if a person walked around the back of the user of an embodiment, the person would notice a series of bright lights following the person from behind and around the embodiment until the threat is gone, and the user may be notified of the presence of the person via a vibrating alert system. This system may be employ existing back and side platforms of the LED or other light display or be part of a light broadcast or other broadcast platform.

In an embodiment, both the vibrating alert system and the reactive light tracking system may be available in mini versions to facilitate installation on motorcycle helmets, bicycle cycling helmets and other headgear, and may be controlled and powered via being hardwired or wireless to a main system.

In an embodiment, a vital-sign tracking system may integrate galvanic skin response (GSP) and sensors to achieve a history of the user vital signs, such as a short history immediately after an accident or fall or a history manually activated by the user, which may be of a default or selected duration. This platform may document the body's temperature, blood pressure, pulse heart rate and respiratory breathing rate if the system is activated. The embodiment could provide a blueprint of the user's vital signs between when the accident occurred and when the EMT Services or Aid Rescuers arrive at the scene of the accident to start life saving measures. Distress or emergency platforms could automatically activate vital-sign tracking. Vital-sign tracking may utilize the sleeve(s) of the garment to allow direct skin contact with the underside of the wrist and either or the collar of the garment to provide direct skin contact to the back of the neck for blood pressure, body temperature and heart rate by metal contacts or skin conductance meters. A jacket, coat or garment may house an expandable chest strip including sensors to obtain information, such as a body temperature, blood pressure, pulse, respiratory breathing rate, etc. The jacket, coat or garment may have to be closed, buttoned up or zipped up in order for the expandable chest strip to work correctly. The jacket chest radius may be much larger than the chest of the body allowing plenty of room for a snug flexible tape strap sensor. Utilizing a snug expandable chest strip would provide the consistent light pressure for the monitor to determine the expansion or inhale and contraction or exhale for proper measurements. The embodiment may keep the information stored digitally or produce a dispensing paper tape stream from a micro-printer out onto the side of the embodiment. This system may be utilized without the paper tape stream to keep track if the user feels the system needs to be turned on for long night trips (for example). In an embodiment, a vital-sign tracking system may facilitate keeping a driver awake by determining if the operator of a motorcycle is falling asleep then waking the driver back up by utilizing an audible alarm, digital voice recording (Hey, Wake-Up!!) and/or a vibrating alert system based on calculating heart rate and breathing cycles and/or skin conductance measurements. An embodiment may use a distance sensor that measures the driver's or user's head perpendicular perspective by installed helmet electro magnets and embodiment electro magnets that measures the difference in polarity field pressures by opposing magnetic fields. An embodiment may employ gyroscopes, MEMS devices, etc., to determine an orientation of a user's head, and activate an alarm based on the determined orientation. For example, if the head of a user droops or the user falls asleep, the alarm, digital recording or vibrating alert system alerts the driver or rider or takes other protective actions (e.g., activating warning displays, brakes, etc.). Thresholds may be employed to determine whether to activate an alarm (e.g., threshold angles, threshold periods of time, etc., and various combinations thereof).

An embodiment may have voice recognition capabilities (e.g., blinker right, blinker left, brake on—brake off, Help, 911, off, stop, override, etc.). Passive listening devices available to the user may be employed by mounting a microphone inside the helmet, existing phone connection or micro-flex microphones, jawbone microphones, etc. These devices may be mounted near the mouth of the user, from a helmet, from the ears, etc. Passive listening devices which pair up independently and separate to the user's cellular phone may be employed. Listening devices in a user's cell phone may be employed. The audio systems could be connected via a wireless system or could be introduced as a separate internal system. Using voice activated switching (VOX) or voice commands instead of or in addition to using simple buttons, knobs, and touch screens should reduce driver distraction times of which could reduce accidents and increase reflex timing.

In an embodiment, a GPS tracker may track the user via Short Message Service (SMS) of other services from anywhere in the world. The embodiment may receive and/or send the coordinates of a user's location and a link, such as a Google Maps link, to the user's location within seconds of tracking confirmation. The GPS tracker would allow following of a user's route for determining mileage or for mapping purposes. GPS tracking may be accompanied by longitude and latitude identifiers along with cross-street triangulation or addresses or vice versa.

In an embodiment, a system may connect to the user's smartphone via Bluetooth™ or other wireless system protocols with the possibilities of a variety of smart features including full design, full lighting controls, turn-by-turn navigation. Embodiments may come equipped with a low-power GPS module that allows you to track your location from anywhere in the world. Associated services could be paid for using a pay-to-use SIM card, digital currency or wireless payment device, etc. In an embodiment, a user may send a text or e-mail message via Short Message Service (SMS) to retrieve or announce the user's location to anyone or generate a ground track. In response, a user may receive an SMS reply containing a link (e.g., a Google Maps™ link) to the user's current location and past track.

An embodiment may determine how far a user is from the user's bike, motorcycle or vehicle while a controller (e.g., controller 104b of FIG. 1) may turn a vehicle system on or off accordingly through wireless communication if desired. In an embodiment, when a user approaches the user's vehicle, the vehicle may automatically turn on, when the user walks away for a determined and adjustable distance, the vehicle may be configured to automatically turn off via wireless range controllability or distance sensors. Some embodiments, for example, for use by police officers, may use communication systems with extended range to facilitate reception at range distance greater than desired for other applications.

In an embodiment, a proximity and perimeter laser guide light may project a basic adjustable lateral finite range area of a visual distance safety laser light zone around onto the ground surface around motorcycles, bicycles or persons. The laser device may be directed downward onto the ground along both sides of the perimeter of the protection device itself. By utilizing lasers mounted inconspicuously to an electronic gyroscopic stabilizer (pitch and yaw) on each side would facilitate an image being projected by the laser that is clearly legible and creates the continual image, solid light line, broken light line, image, design, phrase or street address onto the ground smoothly while surrounding the user with a close safety range, buffer or zone while not blinding oncoming traffic or people not connected to this system. This laser image would appear to be traveling along side and with the embodiment. Integrating a mapping application, such as Google Maps™ may provide address detail in real time as the user travels past a specific street or location to be inscribed onto the ground surface, if desired.

In an embodiment, a compressed air engagement system may provide users the confidence of knowing if they do need the system it completely has them protected. Intergraded inline instantly expandable air tubes that follow the exterior of the body within the embodiment to protect against impact or fall with a protective body of air. This system may employ a semi-ridged plastic or rubber tubing configuration or expandable body plates. The system may be charged by a replaceable set of mini-canisters or mini-cartridges of compressed gas (e.g., air) that would instantaneously fill the tube airlines under the embodiment to protect and minimize the body from injury. The sealed high pressure plastic airlines may be contained within and under the leather, Kevlar, plastic or other fabric jacket, top, pants, etc. Once the cartage is discharged, replacement is simple and easy. For example, if the system determines that a crash is imminent (for example, based on detection of an approaching vehicle, an indication that the user's vehicle is unstable (e.g., information from sensors, such as MEMs devices, indicating the vehicle is likely to crash), a manual activation, etc., the system may deploy the compressed air engagement system to provide the user with an additional air barrier against injury.

An embodiment may also comprise or be connected and expandable to a video system like GoPro™ or another system to record anything and everything as proof of fault in case of an incident. The embodiment may have mounting points available within the system along with a power source and the ability to transmit in real time via the user's cell system or other communication device.

In an embodiment, international navigation position lights—green right, red left and white front and back may be employed, for example, in case primary system is shutdown.

In an embodiment, an LED hot spot generator may provide a platform to expand the continuity of internet or cell reception by using the LED lighting itself as a radiant transceiver or remote or connected antenna. The electromagnet field or static fields could benefit each individual LED platform if working together as an enlarged platform receiver group. This LED generating hot spot could develop a transmit energy and utilize static fields or magnetic fields generated by the lighting system of the embodiment. The embodiment could provide additional network management options for individual link connections or allow multi-users a remote platform to integrate into a Virtual Private Network (VPN).

The various embodiments disclosed herein may be independent accessories for an upgradeable category embodiment, depending, for example, on the requirements and independent power supplies and technology growth sources.

The large back facing lighted surface of an embodiment may be reinforced by placing a safety back shield or ballistic plates between the user's body and the lighted broadcast surface. If more area for electronics is desired, the room needed could easily be achieved by enlarging the back internal portion for the additional component space. In an embodiment, an LED display portion may also provide a heat-sink for the electronics, while also serving as a skid-shield and a rigid back support. An embodiment may be contoured or include one or more contoured portions to fit a person's knee, hip, shoulder, elbow, back, etc., or may be adjustable (e.g., bendable, sizable, etc.) to fit a person's body or parts thereof. For example, a shoulder or elbow LED embodiment may include an aluminum heat sink to absorb heat from the LEDs or other electronics while also providing a safety plate for the user. Such heat-sink/plates may prolong the lifespan of the LEDs and other electronics by reducing the operating temperatures.

Motorcycles sometimes adjust speed through downshifting, versus using only actual brakes in order to activate the brake lights, along with other powered and human powered equipment—motorcycles, Bicycles, ATV's, etc. In an embodiment, a pre-braking alert system may be employed. For example, an indication of a downshift consistent with downshift breaking (e.g., downshifting with increased activation of an accelerator, downshifting while traveling downhill, etc.) may trigger an activation of brake lights or displays. In an embodiment, the pre-braking alert system may be integrated into lighting systems or articles of clothing disclosed elsewhere herein. In an embodiment a pre-braking alert system may be an accessory to a lighting system disclosed herein. Embodiments including pre-braking alert functionality may be employed in powered or non-powered vehicles.

Regarding vehicles that decelerate, perhaps drastically, without physically or manually applying the use of brakes, deceleration speed indicators (e.g., signals from a position or speed sensor, an acceleration sensor, etc.) may be used to activate the brake lighting or slow-down lighting warning indicators as an additional option to notify approaching vehicles from behind of sudden or quick stops prior to actual braking activated light safety lighting (e.g., brake lights).

In some situations motorcycles and other equipment may use engine compression or downshifting to slow down. With bicycles, shifting down may also radically reduce the speed of the equipment without notification of the reduction of speed to those behind. In this situation, the brake lights won't activate thus not activating and alerting those from behind the user as the vehicle is actually slowing down through another speed reducing means (other than physically applying the brakes).

In most motorcycles (for example) the reduction of speed may be drastic even though the brakes won't have been applied until almost actually stopped completely or in a low gear. The concern is getting rear ended or hit from behind because the converging driver from behind cannot determine if the motorcycle is actually slowing down or not. At night, this situation may become increasingly more difficult due to the decreasing ability of depth perception thus increasing inaccuracies in the human eye at night. These nighttime human eye errors would slow reaction time by slowing impulses to the muscles to react since no visual alert notification would be provided.

In an embodiment the reduction of speed and/or speed variations may be detected, for example via GPS, engine compression deceleration sensors, clutch deceleration sensors, clutch sequenced downshifting sensors, transmission or engine RPM variations, radar or through decreasing speedometer speed indicators/sensors. These sensors may be connected as an accessory to the vehicle directly or may be integrated into the article of clothing as a standalone and independent solution with Bluetooth™ or other wireless capabilities or hardwired solutions as an information delivery system to initiate the brake lights or other indicators prior to activating the brake lights and/or prior to physically activating the braking mechanism.

Furthermore, speed reduction detection may be employed for skiers, runners, skateboarders, etc., via a GPS or acceleration detection systems to detect a reduction of speed and initiate warnings (e.g., lights or symbols) in response thereto. In some embodiments, thresholds may be employed (e.g., deceleration thresholds, proximity thresholds, etc.) to determine when to active a speed reduction warning or collision warning (e.g., one or more lights or symbol displays indicating a reduction of speed, alarms indicating a likely collision, etc.).

FIGS. 4 and 4A to 4F are a flow diagram of an example embodiment of a user-protection management routine or method 400 that may be employed by an article of clothing including embedded user-protection circuitry to provide user-protection services. For convenience, the routine 400 will be described with reference to the embodiments of FIGS. 1 and 3. The routine or method 400 may be performed by embodiments other than the system 100 of FIG. 1 and the system 300 of FIG. 3. For convenience, the routine or method 400 will be referred to as routine 400 in this description.

The routine 400 may be provided by, for example, execution of the protection device application manager 324 of FIG. 3, the controller 104 of FIG. 1, etc., such as to provide user-protection and related services.

The illustrated embodiment of the routine 400 begins at block 405, where a request or other information is received. The routine continues to block 410 to determine whether a received request or other information is an indication that a wearer of an article of clothing is stopped, such as an indication from an accelerometer that the wearer is not moving, a stop command, an indication received from a vehicle the wearer is operating that the vehicle is stopped, etc. If so, the routine 400 proceeds to block 412, to broadcast a stop signal (e.g., an indication that the wearer of the article of clothing is stopped, such as an image of a stop sign on a display embedded in the article of clothing, a flashing red-light from one or more LEDs embedded in the article of clothing, etc., such as discussed in more detail elsewhere herein). The routine proceeds from block 412 to block 490.

If it is determined that the received request or other information is not an indication that a wearer of the article of clothing is stopped, the routine proceeds to block 415, where it is determined whether the received request or other information is an indication that the wearer is slowing down or traveling slowly, such as a brake command, an indication received from a vehicle the wearer is operating that the vehicle is slowing down (e.g., a downshift), an indication from an accelerometer that the wearer is moving below a threshold speed, etc. If so, the routine 400 proceeds to block 416, to optionally check other indications of whether a wearer of the article of clothing is slowing down or traveling below a threshold speed. The routine proceeds from block 416 to block 418. At block 418, the routine determines whether the receiving indication and the other indications are consistent with a slowing down or slow speed of a wearer of the article of clothing. For example, if a brake command is received, the routine may determine the wearer is slowing down without regard to other indications, if an indication of a downshift is received, the routine may check whether an acceleration signal is consistent with slowing down, etc. When it is determined that the wearer of the article of clothing is slowing down or traveling at a slow speed, the routine proceeds to block 419 to broadcast a braking or slow signal (e.g., an indication that the wearer of the article of clothing is braking, such as a solid or flashing red image on a display embedded in the article of clothing, a flashing red-light from one or more LEDs embedded in the article of clothing, etc., such as discussed in more detail elsewhere herein). The routine proceeds from block 419 to block 490. When it is determined at block 418 that the wearer is not slowing down or traveling at a slow speed, the routine proceeds to block 490.

If it is determined that the received request or other information is not an indication that a wearer of the article of clothing is slowing down or traveling at a slow speed, the routine proceeds to block 420, where it is determined whether the received request or other information is a configuration request or configuration information. If so, the routine 400 proceeds to block 421, to optionally present a configuration menu. The routine proceeds to block 422 to receive configuration information, such as selections from a configuration menu, and to block 423 to configure the system in accordance with the received configuration information. For example, a user may desire to select a particular response to an indication of a slowing condition, may wish to enable synchronization of the system with user-protection systems of other articles of clothing, may wish to select various modes of operation (e.g., walking mode, bicycling mode, motorcycling mode, traffic control mode, search and rescue mode, crowd control mode, etc.), may wish to return to a default configuration, etc., such as described elsewhere herein. The routine proceeds from block 423 to block 490.

If it is determined that the received request or other information is not a configuration request or configuration information, the routine proceeds to block 425 to determine whether the received request or other information is an indication of an intended turn, such as a left turn or a right turn. If so, the routine 400 proceeds to block 427 to determine a direction of the turn and to block 429 to broadcast an indication of an intended turn in the determined direction, such as displaying an arrow indicating the intended turn on a display embedded in the article of clothing, etc. The routine proceeds from block 429 to block 490.

If it is determined that the received request or other information is not an indication of an intended turn, the routine proceeds to block 430 to determine whether the received request or other information is an indication of a hazard, such as an indication of an approaching vehicle, an indication of a stopped vehicle in a path of a wearer of the article of clothing, an indication of an approaching foe, an indication that a wearer is falling asleep, etc., as described elsewhere herein. If so, the routine 400 proceeds to block 432 to determine the nature of the hazard, and to block 434 to determine an appropriate warning signal to broadcast to the wearer of the article of clothing based on the determined nature of the hazard. For example, if it is determined that the hazard is an approaching vehicle, the determined warning signal may be a physical pulse, a location of the pulse may indicate a direction of approach, a rate of the pulse may indicate a speed of the approach, and a strength of the pulse may indicate whether evasive action should be considered. Silent warning signals may be employed to warn of an approaching foe, noisy warning signals may be employed to warn of inattentive operation of a vehicle, etc., as described elsewhere herein. Look-up tables and threshold values may be employed to determine the nature of a hazard and an appropriate warning signal. The routine proceeds from block 434 to block 436 to broadcast the determined warning signal. The routine proceeds from block 436 to block 490.

If it is determined that the received request or other information is not an indication of a hazard, the routine proceeds to block 440 to determine whether the received request or other information is instruction information, such as an instruction information to a police officer related to a location of a target in a crowd, traffic control information, driving directions, etc., as discussed elsewhere herein. If so, the routine 400 proceeds to block 442 to determine the nature of the instruction information, and to block 444 to determine an appropriate manner to broadcast the instruction information to the wearer of the article of clothing based on the determined nature of the instruction information. For example, if it is determined that the information is related to a location of a target in a crowd to be provided to a police officer, the determined signaling may be a silent signal to notify the police officer without notifying the target. The received information may include other information or additional instructions, such as whether to approach the target or monitor the target, etc. Look-up tables and threshold values may be employed to determine the nature of instruction information and an appropriate manner to broadcast the instruction information to a wearer of the article of clothing, and/or to others, as the case may be. The routine proceeds from block 444 to block 446 to broadcast the instruction information in the determined manner. The routine proceeds from block 446 to block 490.

If it is determined that the received request or other information is not instruction information, the routine proceeds to block 450 to perform one or more other indicated operations as appropriate. Other operations may have various forms in various embodiments, such as one or more of the following non-exclusive list: obtaining or updating information used to provide various services provided by the user-protection manager routine (e.g., error processing; time-out processing (e.g., timing out a selection window presented to a user); file maintenance; processing related to terminating a session; etc. After block 450, the routine continues to block 490 to determine whether to continue, such as until an explicit termination instruction is received. If so, the routine returns to block 405, and if not the routine continues to block 495 and ends.

It will be appreciated that in some embodiments the functionality provided by the routines discussed above may be provided in alternative ways, such as being split among more routines or consolidated into fewer routines. Similarly, in some embodiments, illustrated routines may provide more or less functionality than is described, such as when other illustrated routines instead lack or include such functionality respectively, or when the amount of functionality that is provided is altered. In addition, while various operations may be illustrated as being performed in a particular manner (e.g., in serial or in parallel) and/or in a particular order, in other embodiments the operations may be performed in other orders and in other manners. Similarly, data structures (e.g., a data structure indicating an appropriate response signal to a received indication; a data structure indicating codes corresponding to friends; etc.) may be structured in various manners in other embodiments, such as by having a single data structure split into multiple data structures or by having multiple data structures consolidated into a single data structure, and may store more or less information than is described (e.g., when other data structures instead lack or include such information respectively, or when the amount or types of information that is stored is altered).

Some embodiments may distribute various operations among various components in other manners. For example, in some embodiments an application on a local server may provide services to a user of a user-protection device via a smart phone (see, e.g., smart phone 160 of FIG. 1) which is not executing a user-protection application.

Figure 4:
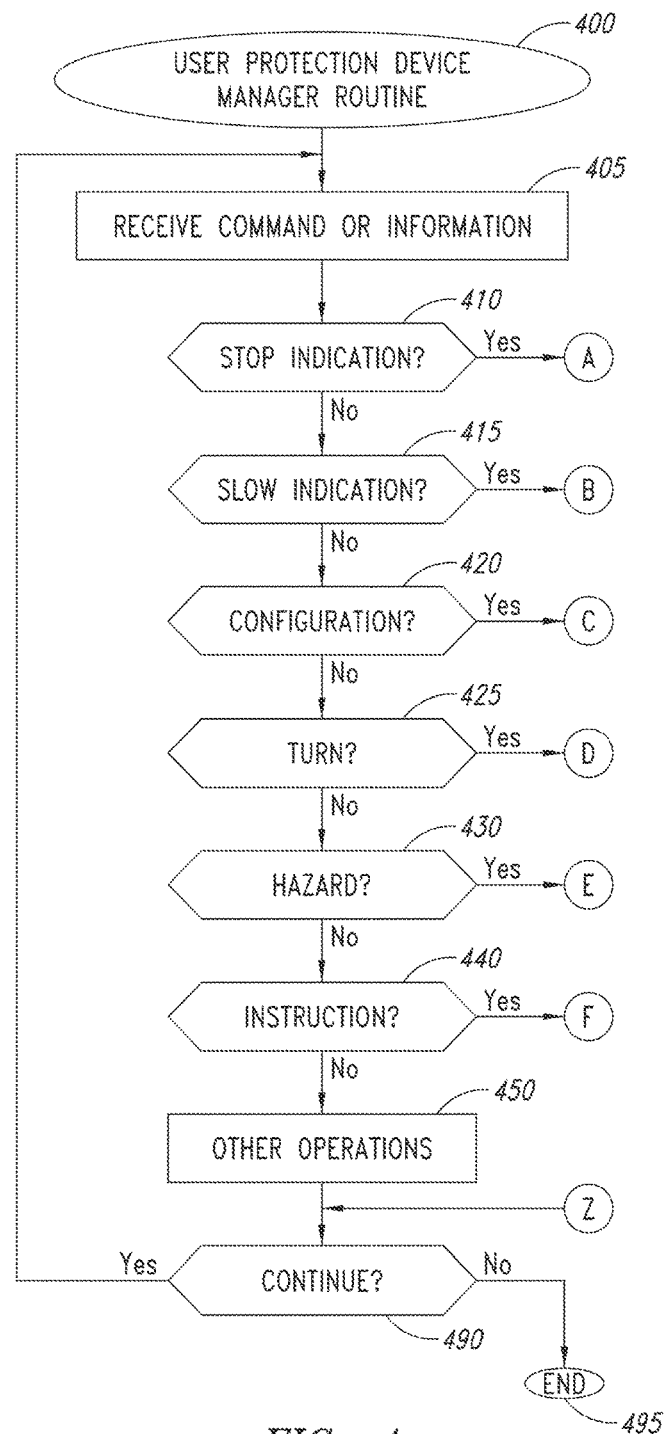
FIGS. 4 to 4F are a flow diagram of an embodiment of a user-protection device manager routine.
Figure 4A:
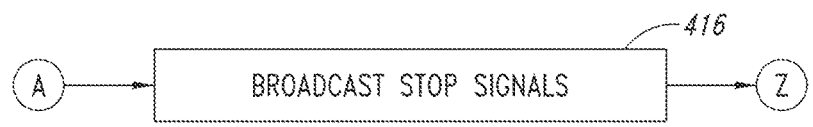
Figure 4B:
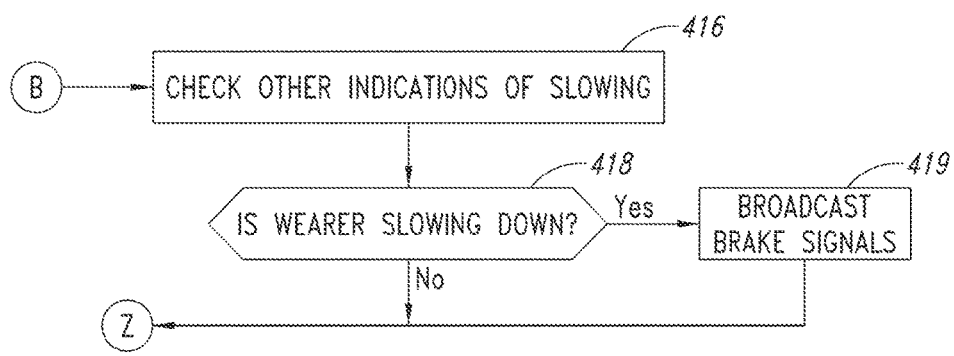
Figure 4C:
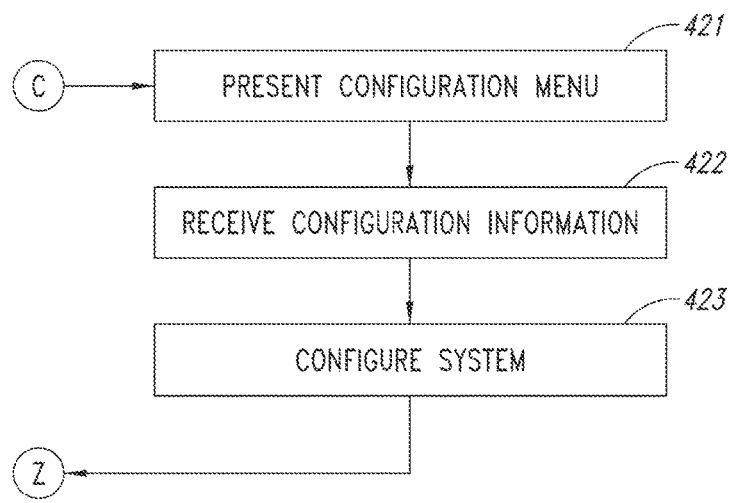
Figure 4D:
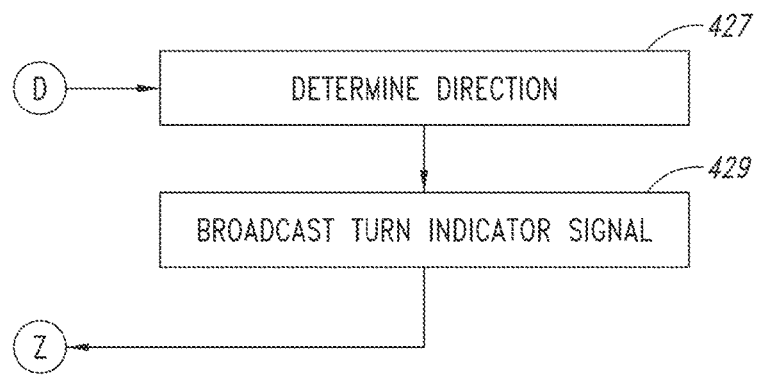
Figure 4E:
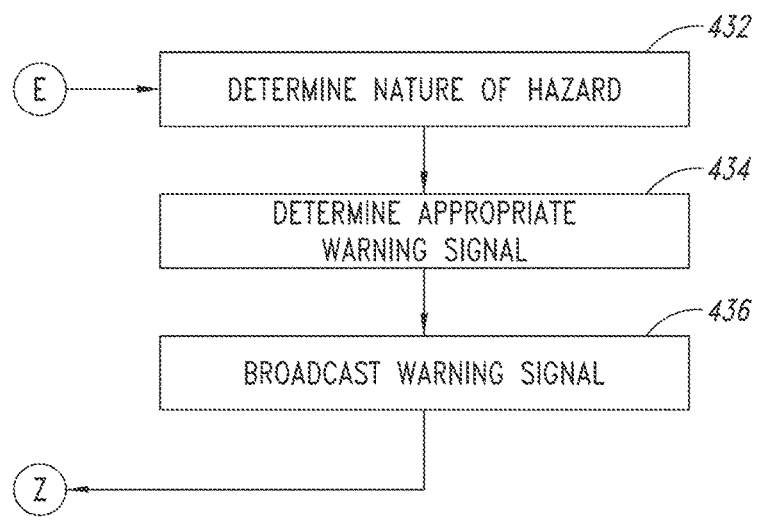
Figure 4F:
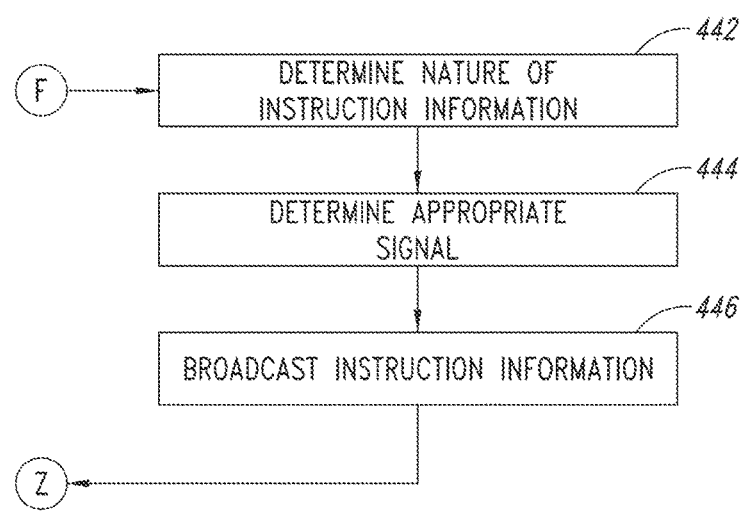

Embodiments of methods of managing a user-protection device may contain additional acts not shown in FIGS. 4-4F, may not contain all of the acts shown in FIGS. 4-4F, may perform acts shown in FIGS. 4-4F in various orders, and may be modified in various respects. For example, time-out routines may be employed. For example, if at block 422 a user fails to make a selection within a threshold time period, the method may proceed to act 490.

Some embodiments may take the form of or comprise computer program products. For example, according to one embodiment there is provided a computer readable medium comprising a computer program adapted to perform one or more of the methods or functions described above. The medium may be a physical storage medium such as for example a Read Only Memory (ROM) chip, or a disk such as a Digital Versatile Disk (DVD-ROM), Compact Disk (CD-ROM), a hard disk, a memory, a network, or a portable media article to be read by an appropriate drive or via an appropriate connection, including as encoded in one or more barcodes or other related codes stored on one or more such computer-readable mediums and being readable by an appropriate reader device.

Furthermore, in some embodiments, some or all of the methods and/or functionality may be implemented or provided in other manners, such as at least partially in firmware and/or hardware, including, but not limited to, one or more application-specific integrated circuits (ASICs), digital signal processors, discrete circuitry, logic gates, standard integrated circuits, controllers (e.g., by executing appropriate instructions, and including microcontrollers and/or embedded controllers), field-programmable gate arrays (FPGAs), complex programmable logic devices (CPLDs), etc., as well as devices that employ RFID technology, and various combinations thereof. For example, embodiments of a article of clothing incorporating a display may be implemented as discussed above (e.g., partially in hardware, partially with controllers executing instructions, etc.).

The various embodiments described above can be combined or split to provide further embodiments. For example, a physical pulse notification embodiment (e.g., a police discrete threat detection and notification embodiment) may be provided alone, or in combination with a visual notification embodiment (e.g., a traffic control embodiment). These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system, comprising:
   an article of clothing; and
   user-protection circuitry, integrated into the article of clothing, the user-protection circuitry including:
   condition-detection circuitry, which, in operation, generates one or more indications related to an environment of the article of clothing;
   pulsing circuitry; and
   control circuitry, which, in operation, activates the pulsing circuitry based on the one or more indications related to the environment of the article of clothing generated by the condition-detection circuitry, wherein the user-protection circuitry, in operation, silently broadcasts information to a wearer of the article of clothing, and the activating the pulsing circuitry comprises activating one or more pulsers in a pattern indicating to a wearer of the article of clothing at least one of:
   identification information related to one or more individuals;
   location information related to one or more individuals;
   movement information related to one or more individuals;
   information related to one or more hazards in a vicinity of the wearer of the article of clothing; and information providing instructions to the wearer of the article of clothing.

2. The system of claim 1, comprising a wireless interface coupled to the user-protection circuitry.

3. The system of claim 1, comprising a control terminal, which, to operation, transmits control signals to the user-protection circuitry.

4. The system of claim 1 wherein, in operation, the control circuitry configures the user-protection circuitry based on control signals received by the system.

5. The system of claim 1 wherein the user-protection circuitry comprises one or more of:
one or more displays;
one or more light emitting diodes (LEDs);
one or more pulsers;
one or more lasers; and
one or more speakers.

6. The system of claim 1 wherein the pulsing circuitry includes one or more physical-impulse pulsers and silently broadcasts information to a wearer of the article of clothing by activating the one or more physical impulse pulsers.

7. The system of claim 1 wherein the condition-detection circuitry comprises one or more of:
an accelerometer;
a braking-condition sensor;
a temperature sensor;
a MEMS device;
a microphone;
a switch;
a pulse-detector;
an image capture device; and
a communication interface.

8. The system of claim 1, comprising:
a second article of clothing, which, in operation, communicatively couples to the user-protection circuitry.

9. The system of claim 8 wherein the second article of clothing comprises at least one of:
condition-detection circuitry, which, in operation, generate one or more indications related to an environment of the second article of clothing; and
broadcast circuitry.

10. The system of claim 1 wherein the broadcast circuitry, in operation, broadcasts, one or more of:
a symbol indicating a braking condition of a wearer of the article of clothing;
a symbol indicating a turning direction of the wearer of the article of clothing;
a visual indication of a hazard;
an indication of tracking of an approaching hazard;
a symbol indicating a stop condition;
instructions to one or more individuals approaching a wearer of the article of clothing.

11. A system, comprising:
an article of clothing; and
user-protection circuitry, integrated into the article of clothing, the user-protection circuitry including:
condition-detection circuitry, which, in operation, generates one or more indications related to an environment of the article of clothing;
pulsing circuitry; and
control circuitry, which, in operation, activates the pulsing circuitry based on the one or more indications related to the environment of the article of clothing generated by the condition-detection circuitry, wherein the activating the pulsing circuitry comprises activating one or more pulses in a pattern to indicate whether one or more individuals have been determined to be a friend or a foe of the wearer.

12. The system of claim 11 wherein the user-protection circuitry, in operation, silently broadcasts information to a wearer of the article of clothing.

13. A system, comprising:
an article of clothing; and
user-protection circuitry, integrated into the article of clothing, the user-protection circuitry including:
condition-detection circuitry, which, in operation, generates one or more indications related to an environment of the article of clothing;
pulsing circuitry; and
control circuitry, which, in operation, activates the pulsing circuitry based on the one or more indications related to the environment of the article of clothing generated by the condition-detection circuitry, wherein, in operation, the article of clothing is worn by a first user and the user-protection circuitry coordinates broadcasting of information with user-protection circuitry of another article of clothing worn by a second user.

14. An article of clothing, comprising:
means for generating one or more indications related to an environment of the article of clothing;
means for pulsing;
means for controlling the means for pulsing based on the generated one or more indications related to the environment of the article of clothing; and
means for broadcasting, wherein the means for broadcasting broadcasts information indicating one or more of:
identification information related to one or more individuals;
location information related to one or more individuals;
information related to one or more hazards;
information providing instructions to a wearer of the article of clothing; and
information to one or more individuals approaching the wearing of the article of clothing related to the environment of the article of clothing.

15. The article of clothing of claim 14, wherein the means for broadcasting includes one or more of:
one or more displays;
one or more light emitting diodes (LEDs);
one or more pulsers;
one or more lasers; and
one or more speakers.

16. The article of clothing of claim 14 wherein the indications related to the environment of the article of clothing indicate one or more of:
a speed of a vehicle associated with a wearer of the article of clothing;
a slowing of the vehicle; and
an intended course of the vehicle.

17. A method, comprising:
generating one or more control signals indicative of an environment of an article of clothing;
receiving a wireless communication via a wireless communication interface embedded in the article of clothing; and
controlling user-protection circuitry embedded in the article of clothing based on the generated one or more control signals, the user protection circuitry including one or more pulsing devices, wherein at least one of the one or more control signals is generated based on the received communication, the user-protection circuitry includes broadcast circuitry, the method comprises configuring the broadcast circuitry based on control signals received by the user-protection circuitry, the broadcast circuitry includes one or more pulsers and the controlling the user-protection circuitry comprises activating the one or more pulsers in a pattern indicating to a wearer of the article of clothing at least one of:

identification information related to one or more individuals;

location information related to one or more individuals;

information related to one or more hazards in a vicinity of the wearer of the article of clothing; and information providing instructions to the wearer of the article of clothing.

18. The method of claim 17, comprising generating at least one of the one or more control signals using a sensor embedded in the article of clothing.

19. The method of claim 17 wherein controlling the user-protection circuitry comprises one or more of:
displaying information on a display;
activating one or more light emitting diodes (LEDs);
activating one or more physical pulsers;
activating one or more lasers; and
broadcasting audio on one or more speakers.

20. The method of claim 17 wherein controlling the user-protection circuitry comprises silently broadcasting information to a wearer of the article of clothing.

21. The method of claim 17 wherein the generating one or more control signals comprises one or more of:
generating an indication of an acceleration;
detecting a braking-condition;
sensing a temperature;
receiving motion information from a MEMS device;
receiving sound information from a microphone;
receiving a signal from a switch;
detecting a pulse;
receiving signals from a image capture device; and
receiving signals from a communication interface.

22. The method of claim 17 wherein the article of clothing is worn by a first user and the user-protection circuitry coordinates broadcasting of information with user-protection circuitry of another article of clothing worn by a second user.

23. The method of claim 17 wherein the user-protection circuitry, in operation, broadcasts, one or more of:

a symbol indicating a braking condition of a wearer of the article of clothing;
a symbol indicating a turning direction of the wearer of the article of clothing;
a visual indication of a hazard;
an indication of tracking of an approaching hazard;
a symbol indicating a stop condition;
instructions to one or more individuals approaching a wearer of the article of clothing.

24. A method, comprising:
generating one or more control signals indicative of an environment of an article of clothing;
controlling user-protection circuitry embedded in the article of clothing based on the generated one or more control signals, the user protection circuitry including one or more pulsing devices; and
broadcasting information indicating whether one or more individuals have been determined to be a friend or a foe of a wearer of the article of clothing.

25. A method, comprising:
generating one or more control signals indicative of an environment of an article of clothing;
controlling user-protection circuitry embedded in the article of clothing based on the generated one or more control signals, the user protection circuitry including one or more pulsing devices; and
communicatively coupling user-protection circuitry of the article of clothing to user-protection circuitry of another article of clothing.

26. The method of claim 25, comprising receiving a communication via a communication interface embedded in the article of clothing, wherein at least one of the one or more control signals is generated based on the received communication.

27. The method of claim 26 wherein the received communication is a wireless communication received via a wireless communication interface embedded in the article of clothing.

28. The method of claim 25 wherein the another article of clothing comprises at least one of:
condition-detection circuitry, which, in operation, generate one or more indications related to an environment of the second article of clothing; and
broadcast circuitry.

* * * * *